(12) United States Patent
Li et al.

(10) Patent No.: US 10,351,773 B2
(45) Date of Patent: Jul. 16, 2019

(54) LIQUID CRYSTAL COMPOUNDS OF CYCLOALKYL-CONTAINING DIBENZOFURAN DERIVATIVES, PREPARATION METHOD THEREFOR AND USE THEREOF

(71) Applicant: Shijiazhuang Chengzhi Yonghua Display Material Co., Ltd, Shijiazhuang, Hebei Prov. (CN)

(72) Inventors: Ming Li, Shijiazhuang (CN); Hongru Gao, Shijiazhuang (CN); Fangmiao Zhang, Shijiazhuang (CN); Jingsong Meng, Shijiazhuang (CN); Guoliang Yun, Shijiazhuang (CN); Xing Zhang, Shijiazhuang (CN); Lei Zhao, Shijiazhuang (CN); Jia Deng, Shijiazhuang (CN)

(73) Assignee: SHIJIAZHUANG CHENGZHI YONGHUA DISPLAY MATERIAL CO., LTD, Shijiazhuang, Hebei Prov. (CN)

( * ) Notice: Subject to any disclaimer, the term of this patent is extended or adjusted under 35 U.S.C. 154(b) by 0 days.

(21) Appl. No.: 15/782,133

(22) Filed: Oct. 12, 2017

(65) Prior Publication Data
US 2018/0112132 A1    Apr. 26, 2018

(30) Foreign Application Priority Data
Oct. 21, 2016   (CN) .......................... 2016 1 0916616

(51) Int. Cl.
C09K 19/30    (2006.01)
C09K 19/34    (2006.01)
(Continued)

(52) U.S. Cl.
CPC ........ *C09K 19/3405* (2013.01); *C07D 307/91* (2013.01); *C09K 19/3028* (2013.01);
(Continued)

(58) Field of Classification Search
CPC ..................................................... C09K 19/12
See application file for complete search history.

(56) References Cited

U.S. PATENT DOCUMENTS

2015/0259602 A1    9/2015 Reiffenrath et al.

FOREIGN PATENT DOCUMENTS

CA            2338740 A1 *  2/2000  ............. A61K 31/00
CN      106883861 A  *  6/2017
(Continued)

*Primary Examiner* — Chanceity N Robinson
(74) *Attorney, Agent, or Firm* — Muncy, Geissler, Olds & Lowe, P.C.

(57) ABSTRACT

Disclosed are liquid crystal compounds of cycloalkyl-containing dibenzofuran derivatives, a preparation method therefor and use thereof. The compounds are as represented by formula I. In the molecular structures of the compounds of formula I provided by the present invention, liquid crystal compounds of cycloalkyl terminal group-containing dibenzofuran derivatives, compared with those having flexible alkyl chains as terminal groups, exhibit better intersolubility, and thus the use of a compound as represented by formula I provided by the present invention can improve the intersolubility of a liquid crystal compound and extend the application range of a liquid crystal mixture, producing an important application value.

(Continued)

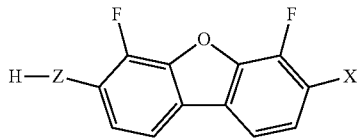

9 Claims, 1 Drawing Sheet

(51) Int. Cl.
*C07D 307/91* (2006.01)
*C09K 19/32* (2006.01)
*C09K 19/04* (2006.01)
*C09K 19/12* (2006.01)
*C09K 19/18* (2006.01)

(52) U.S. Cl.
CPC ........ C09K 19/3066 (2013.01); C09K 19/322 (2013.01); *C09K 2019/0407* (2013.01); *C09K 2019/0414* (2013.01); *C09K 2019/123* (2013.01); *C09K 2019/181* (2013.01); *C09K 2019/301* (2013.01); *C09K 2019/3004* (2013.01); *C09K 2019/3009* (2013.01); *C09K 2019/3016* (2013.01); *C09K 2019/3027* (2013.01); *C09K 2019/3063* (2013.01); *C09K 2019/3077* (2013.01); *C09K 2019/3078* (2013.01); *C09K 2019/3408* (2013.01)

(56) References Cited

FOREIGN PATENT DOCUMENTS

CN 106883862 A * 6/2017
WO WO 00/06082 A1 * 2/2000

* cited by examiner

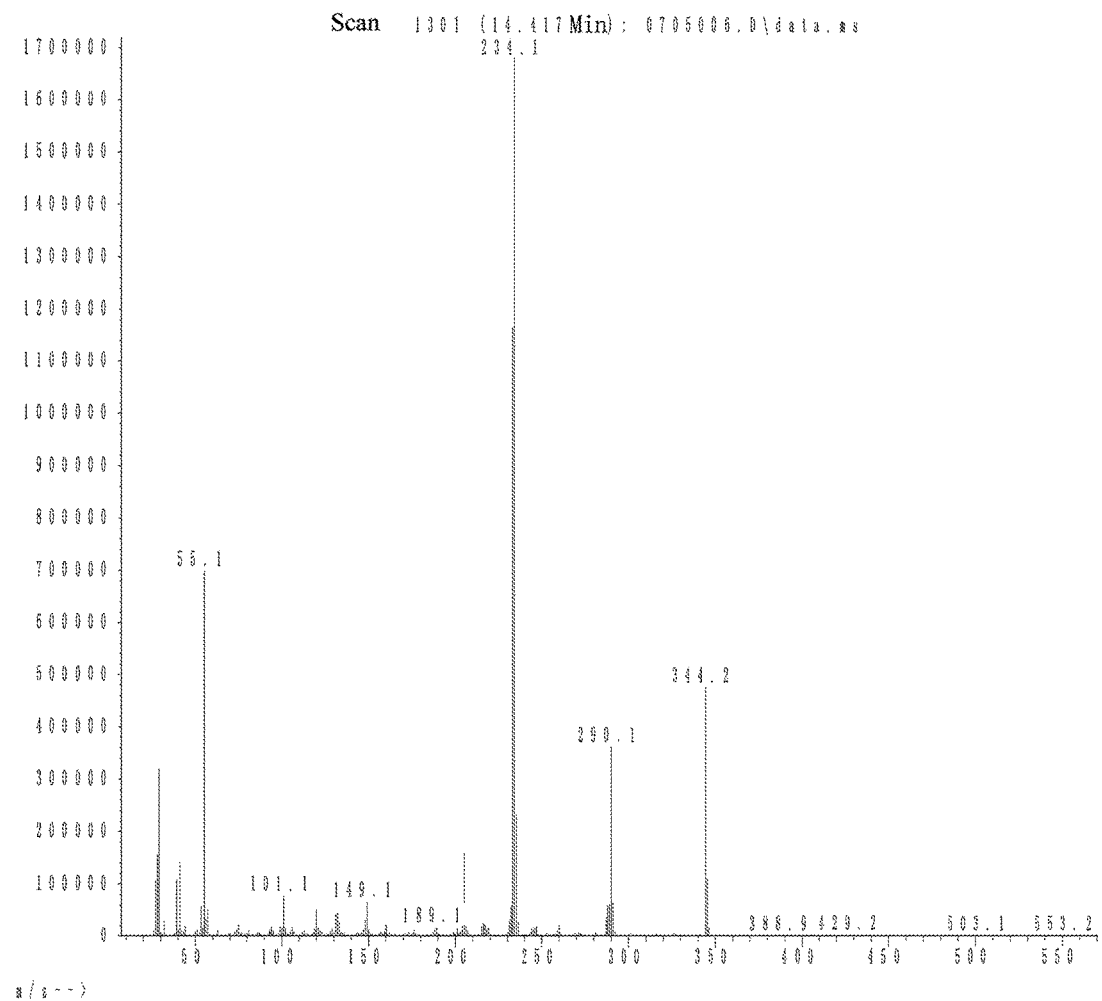

LIQUID CRYSTAL COMPOUNDS OF CYCLOALKYL-CONTAINING DIBENZOFURAN DERIVATIVES, PREPARATION METHOD THEREFOR AND USE THEREOF

TECHNICAL FIELD

The present invention belongs to the technical field of liquid crystal compounds and applications, and relates to liquid crystal compounds of cycloalkyl-containing dibenzofuran derivatives, a preparation method therefor and use thereof.

BACKGROUND ART

Since the Austrian scientist Reinitzer first synthesized a liquid crystal in 1888, the actual development of the liquid crystal industry is in the recent more than 30 years; since liquid crystal display materials have obvious advantages, such as a low drive voltage, a small power consumption, high reliability, a great display information amount, color display, no flicker, a capability of achieving panel display, etc., both liquid crystal monomers and liquid crystal displays have gone through a huge development, and liquid crystal monomers have been used in the synthesis of more than 10,000 kinds of liquid crystal materials, wherein there are thousands of common liquid crystal display materials, and by the classification according to the characteristics of the central bridge bond and rings of liquid crystal molecules, there are mainly biphenyl liquid crystals, phenyl cyclohexane liquid crystals, ester liquid crystals, alkynes, difluoromethoxy bridge types, ethane types and heterocyclic types. The liquid crystal display is also developed from TN and STN of black and white small screen in 30 years ago to the current TN-TFT, VA-TFT, IPS-TFT, PDLC of scale color screen, etc.

New liquid crystal display modes mainly include optical compensation bending mode (OCB), coplanar transformation liquid crystal display (IPS), vertical alignment mode (VA), axisymmetric microstructure liquid crystal display (ASM), multi-domain twisted liquid crystal display, etc.

In the various display modes, liquid crystal cells have different designs and different driving methods, and the orientations of liquid crystal molecular directors with respect to glass substrates are different, wherein in the optical compensation bending mode (OCB) and the coplanar transformation liquid crystal display (IPS), liquid crystal molecular directors are parallel to the direction of the glass substrates, while in the vertical alignment mode (VA) and the axisymmetric microstructure liquid crystal display (ASM), the liquid crystal molecular directors are perpendicular to the direction of the glass substrates in the absence of an electric field.

With regard to the IPS of the parallel arranged mode, the dielectric anisotropy ($\Delta\varepsilon$) of the crystal may be either positive or negative.

In the vertical alignment mode (VA), all liquid crystal molecules in a null field are perpendicular to the direction of the glass substrates and parallel to a vertical incident light. When a polarizer is orthogonal, a good dark state is shown; therefore, this kind of device has a good contrast, and the dielectric anisotropy ($\Delta\varepsilon$) of the crystal used has to be negative. The optical anisotropy ($\Delta n$) of the crystal, the thickness (d) of the liquid crystal cell and the wavelength ($\lambda$) of the incident light barely affect the contrast. The response time of the vertical alignment mode (VA) is much shorter than that of a twist-type device and is about half of that. Under the influence of an applied voltage, a VA device mainly produces a bending deformation of liquid crystal molecules, ECB produces a splay deformation of liquid crystal molecules, and the twisted display produces a twist deformation of liquid crystal molecules; the response times thereof are also inversely proportional to bending, splay, and twist elastic constants, respectively, because in general cases for most liquid crystals, the bending elastic constant of liquid crystal is greater than the splay elastic constant and the splay elastic constant is greater than the twist elastic constant, which is also the reason why the VA device has a faster response time.

In Patent US 20150259602, the following compound is disclosed:

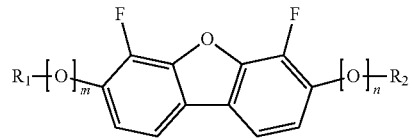

wherein R' and R" represent alkyl groups. Since the presence of the two side fluorines and the rigid structure dibenzofuran in the molecule limits the deflection between the two benzene rings, this type of compound has a higher absolute value of dielectric anisotropy and a very high birefringence. However, also because of the presence of the rigid dibenzofuran ring, such an alkyl-substituted liquid crystal compound has a poorer intersolubility and readily precipitates at low temperatures. In order to enable the performance of a display device to be closer to ideal, people have always been working to study new liquid crystal compounds, which allows the performances of liquid crystal compounds and display devices to continuously advance.

SUMMARY OF THE INVENTION

In order to solve the above-mentioned technical problems, the present invention provides liquid crystal compounds of cycloalkyl-containing dibenzofuran derivatives, a preparation method therefor and use thereof.

The liquid crystal compounds of cycloalkyl-containing dibenzofuran derivatives provided by the present invention have a general structural formula as shown by formula I,

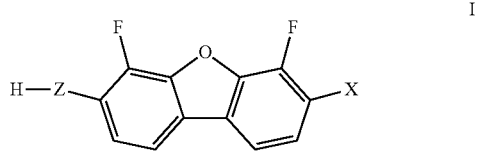

wherein H represents one of cyclopropyl, cyclobutyl, cyclopentyl or 2-tetrahydrofuranyl; Z represents one of a single bond, —CH$_2$—, —O—, —CH$_2$CH$_2$— or —CH$_2$O—; and X represents a hydrogen atom, a fluorine atom, an alkyl group having 1-7 carbon atoms or an alkoxy group having 1-7 carbon atoms.

The compounds as represented by said formula I are preferably compounds as represented by formulas I1 to I15:

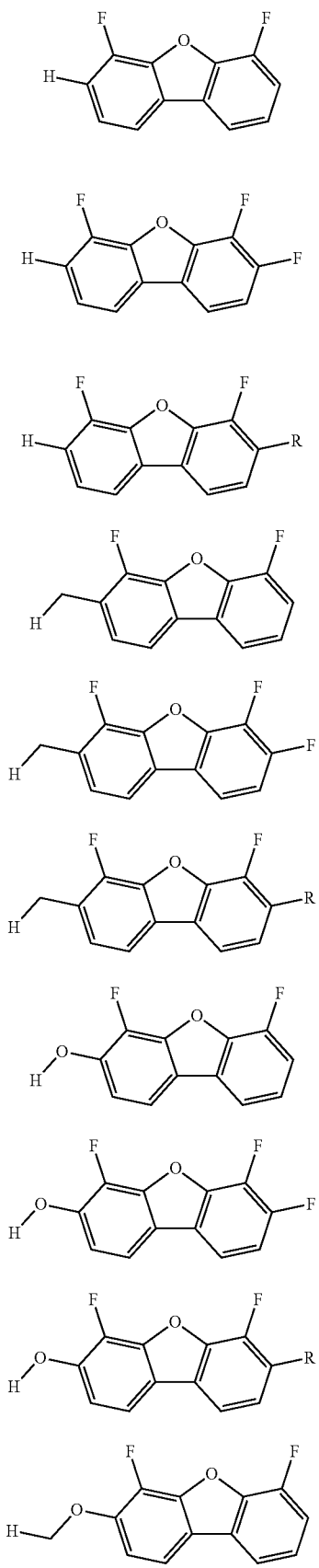
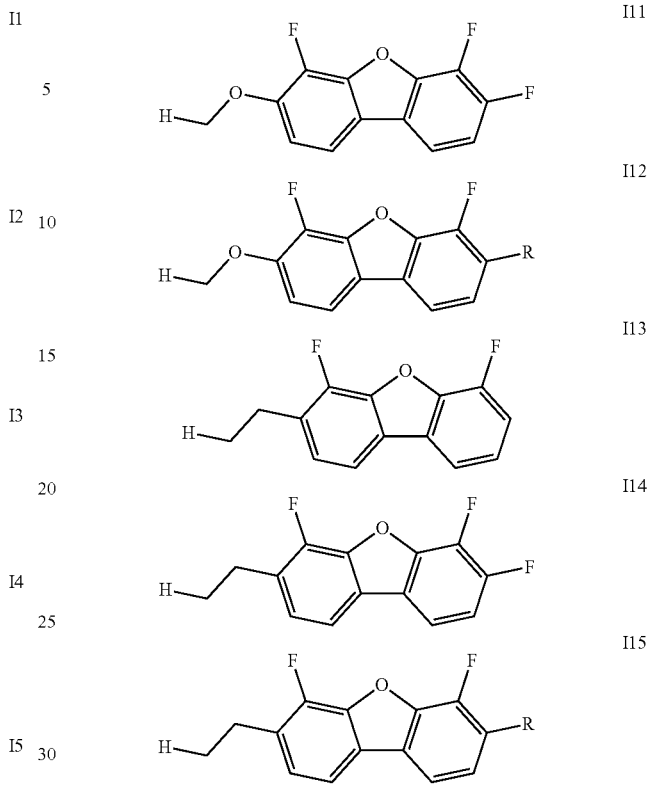
wherein H each independently represents cyclopropyl, cyclobutyl or 2-tetrahydrofuranyl; and R each independently represents an alkyl group having 1-7 carbon atoms or an alkoxy group having 1-7 carbon atoms.
The compounds as represented by said formula I are specifically and preferably the following compounds as represented by I1-1 to I15-2:
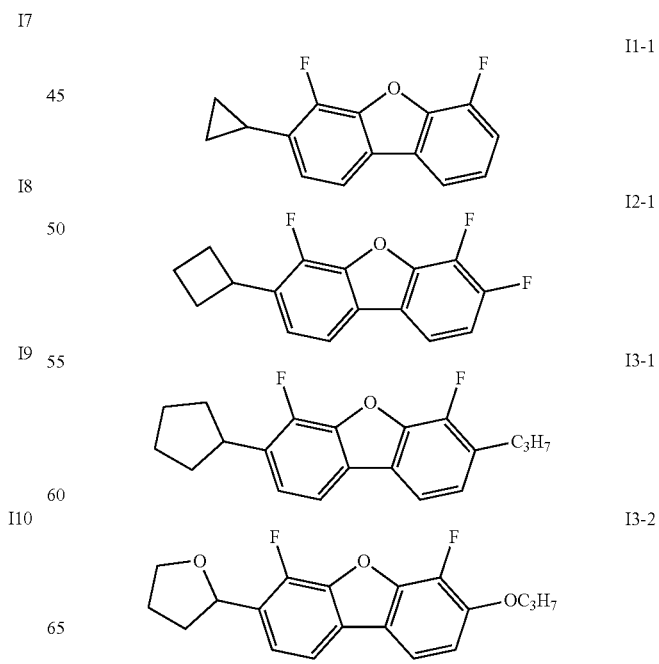

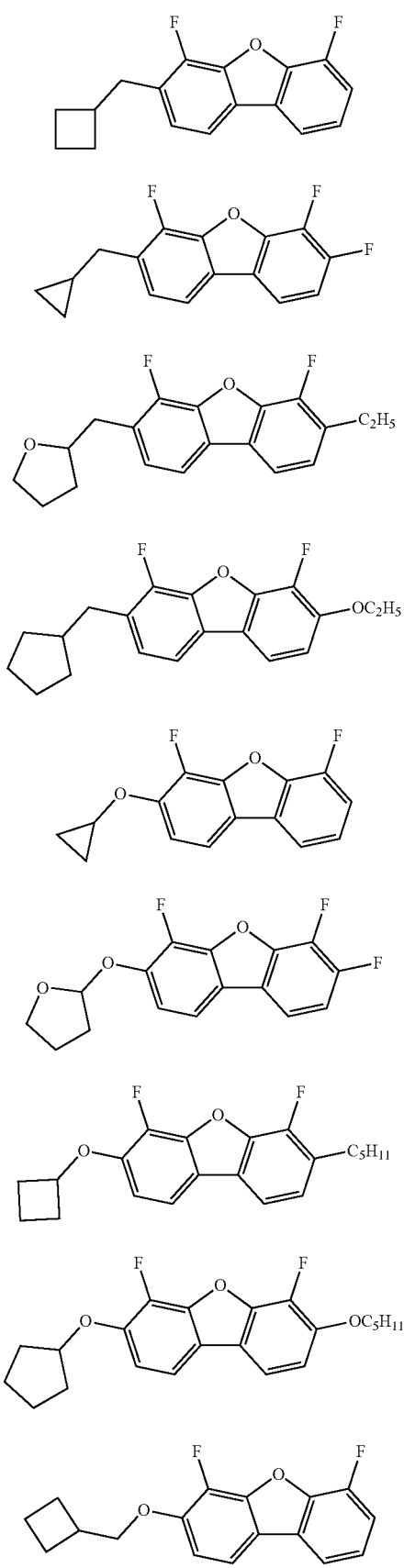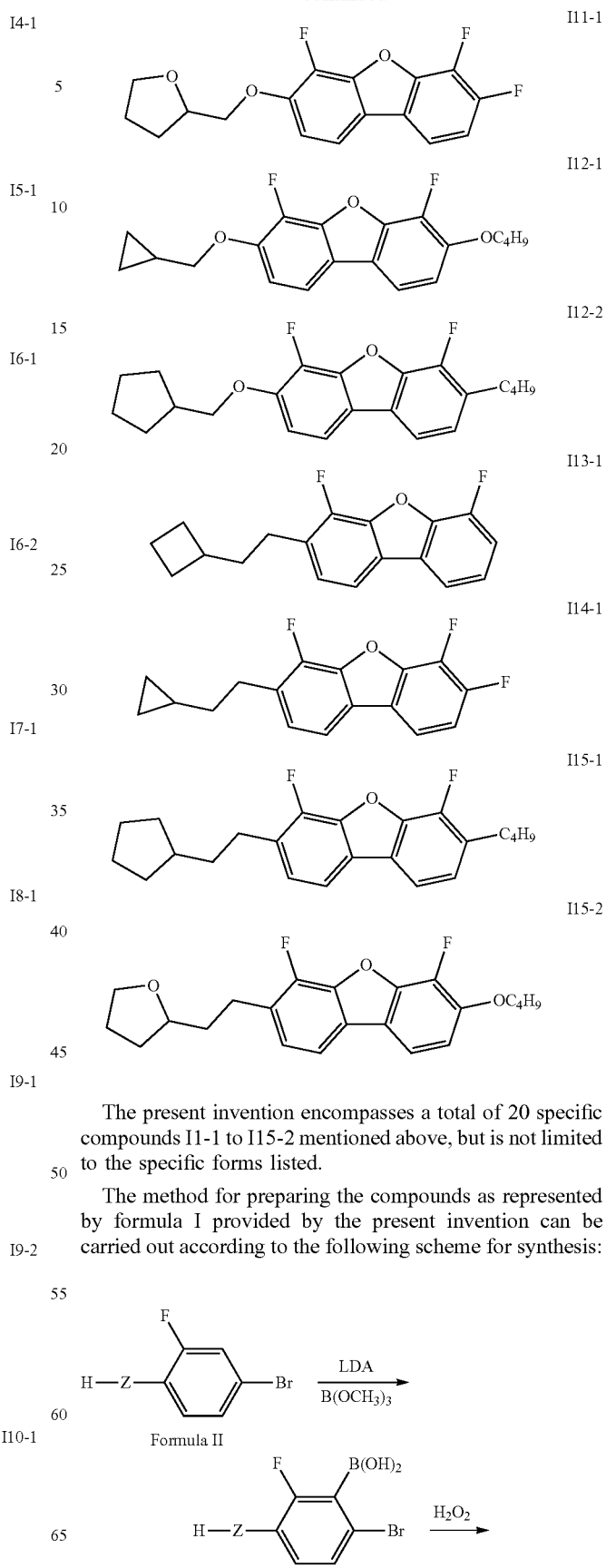
The present invention encompasses a total of 20 specific compounds I1-1 to I15-2 mentioned above, but is not limited to the specific forms listed.
The method for preparing the compounds as represented by formula I provided by the present invention can be carried out according to the following scheme for synthesis:
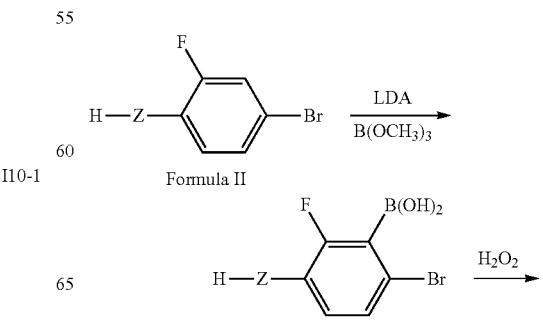

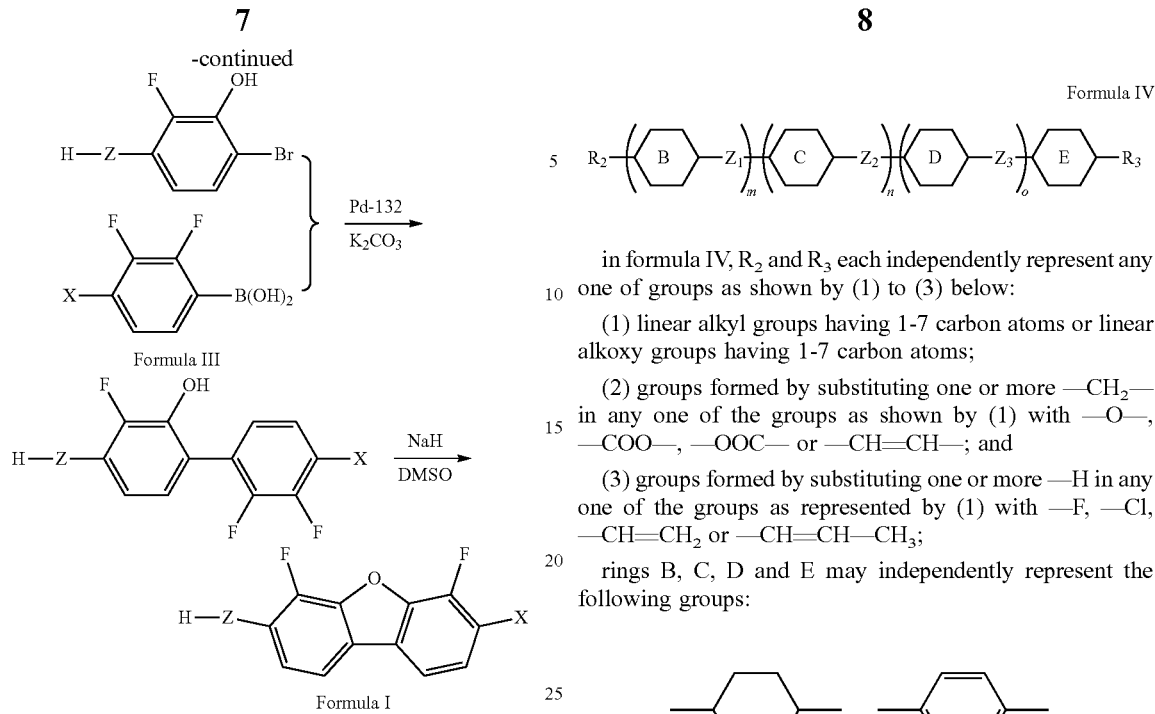

Formula III

Formula I

According to the synthetic route shown in the scheme, formulas II and formula III are key intermediates for the synthesis of the target compound.

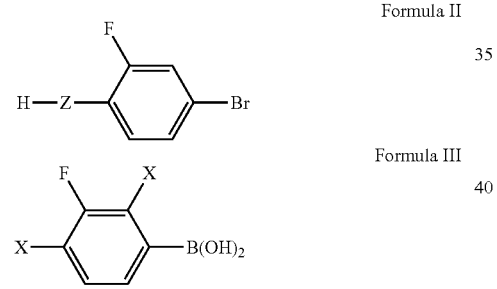

Formula II

Formula III

The key intermediate formulas II and III for the synthesis of the compounds as so represented by general formula I are commercially available, and the principles of such methods, operation procedures, conventional post-treatment, silica gel column chromatography, recrystallization and other means are well known to a person skilled in the art, and can fully achieve the synthesis process so as to obtain the target product.

The reactions of all the steps of all the methods mentioned above are carried out in a solvent; Said solvent is selected from at least one of tetrahydrofuran, N,N-dimethylformamide, ethanol, methanol, dichloromethane, acetone, toluene and deionized water.

The present invention further provides a liquid crystal medium characterized in that said liquid crystal medium comprises one or more compounds as represented by said structural formula I.

Said liquid crystal medium may further comprise one or more compounds of the liquid crystal compounds as represented by structural formula IV, as a second component:

Formula IV $$R_2 -\left(\!\left(B\right)\!-Z_1\right)_m\!\left(\!\left(C\right)\!-Z_2\right)_n\!\left(\!\left(D\right)\!-Z_3\right)_o\!\left(E\right)\!-R_3$$

in formula IV, $R_2$ and $R_3$ each independently represent any one of groups as shown by (1) to (3) below:

(1) linear alkyl groups having 1-7 carbon atoms or linear alkoxy groups having 1-7 carbon atoms;

(2) groups formed by substituting one or more —$CH_2$— in any one of the groups as shown by (1) with —O—, —COO—, —OOC— or —CH=CH—; and (3) groups formed by substituting one or more —H in any one of the groups as represented by (1) with —F, —Cl, —CH=$CH_2$ or —CH=CH—$CH_3$;

rings B, C, D and E may independently represent the following groups:

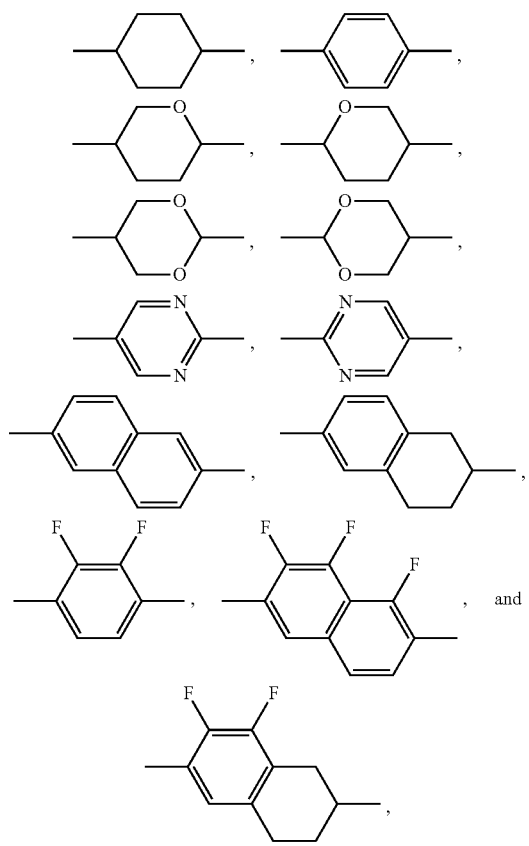

and at least one is selected from

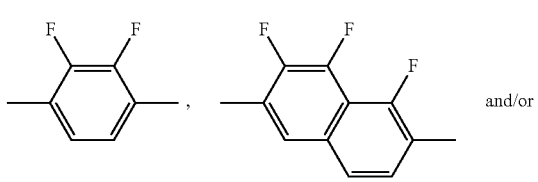

and/or

-continued

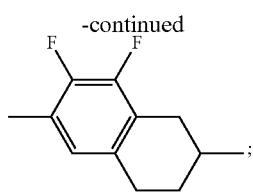

m, n and o each independently represent 0 or 1;
$Z_1$, $Z_2$ and $Z_3$ each independently represent a single bond, —$C_2H_4$—, —CH=CH—, —≡—, —COO—, —OOC—, —$CH_2O$—, —$OCH_2$—, —$CF_2O$—, or —$OCF_2$—, wherein any H atom may be replaced with F.

Further, the liquid crystal medium provided by the present invention may further comprise one or more compounds as represented by structural formula V, as a third component,

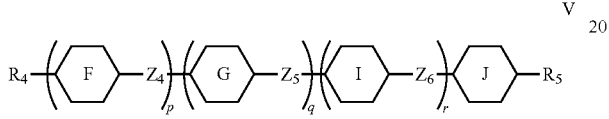

V in said formula V, $R_4$ and $R_5$ each independently represent an alkyl group having 1-10 carbon atoms or an alkenyl group having 2-10 carbon atoms; in addition, any —$CH_2$— of these groups may be replaced with —$CH_2O$—, —$OCH_2$— or —C≡C—, and any hydrogen may be replaced with F;

rings F, G, I and J each independently represent the following groups:

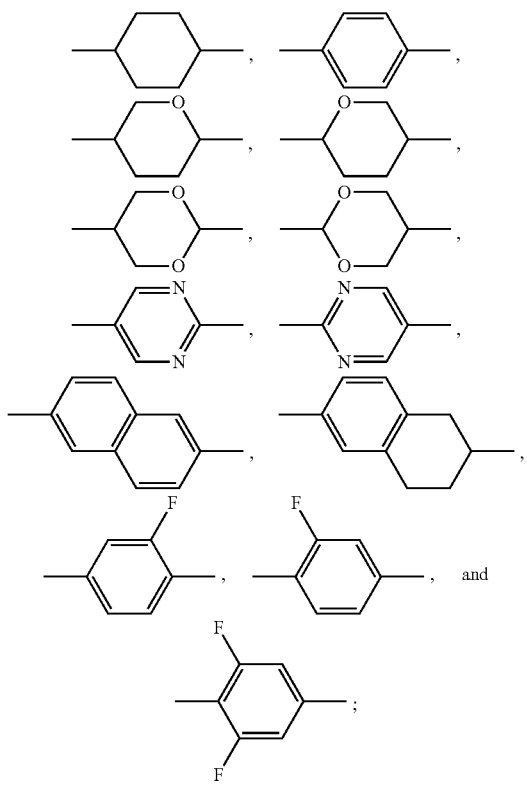

p, q and r each independently represent 0 or 1;
$Z_4$, $Z_5$ and $Z_6$ each independently represent a single bond, —$C_2H_4$—, —CH=CH—, —≡—, —COO—, —OOC—, —$CH_2O$—, —$OCH_2$—, —$CF_2O$—, or —$OCF_2$—, wherein any H atom may be replaced with F.

The compound as represented by formula IV is preferably selected from one or more of the following compounds:

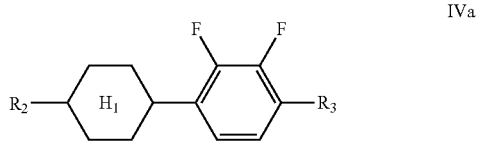

IVa

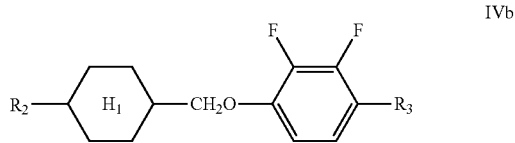

IVb

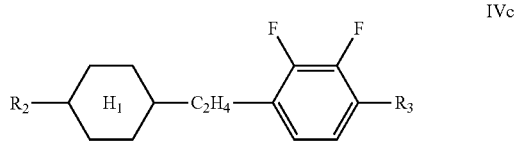

IVc

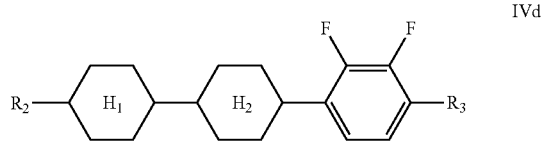

IVd

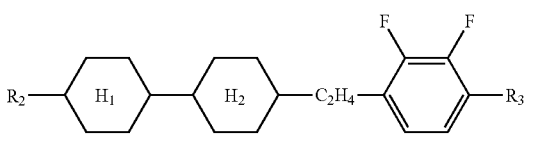

IVe

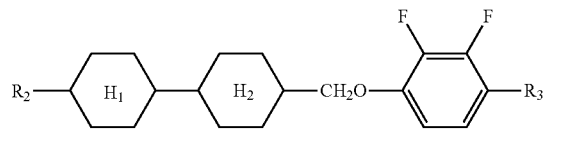

IVf

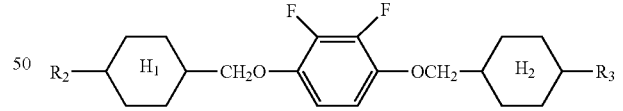

IVg

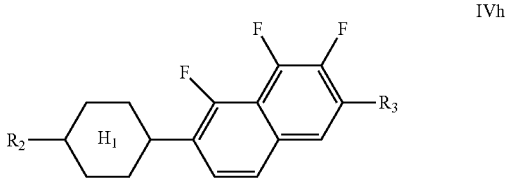

IVh

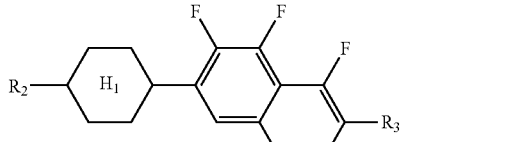

IVi

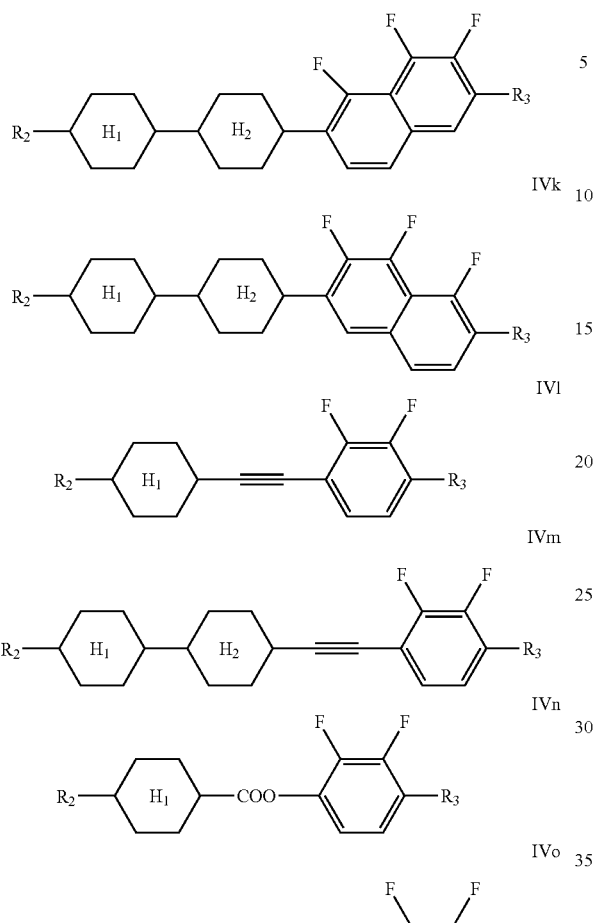

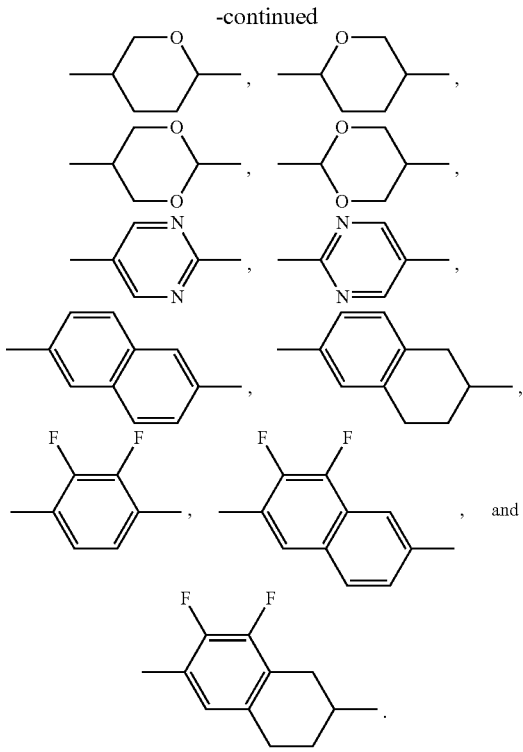

wherein $R_2$ and $R_3$ each independently represent any one of groups as shown by (1) to (3) below:

(1) linear alkyl groups having 1-7 carbon atoms or linear alkoxy groups having 1-7 carbon atoms;

(2) groups formed by substituting one or more —$CH_2$— in any one of the groups as shown by (1) with —O—, —COO—, —OOC— or —CH=CH—; and (3) groups formed by substituting one or more —H in any one of the groups as represented by (1) with —F, —Cl, —CH=$CH_2$ or —CH=CH—$CH_3$;

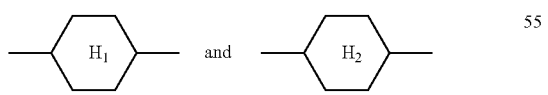

each independently represent any one of the following groups:

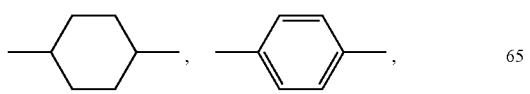

The compound as represented by structural formula V is preferably selected from one or more of the following compounds:

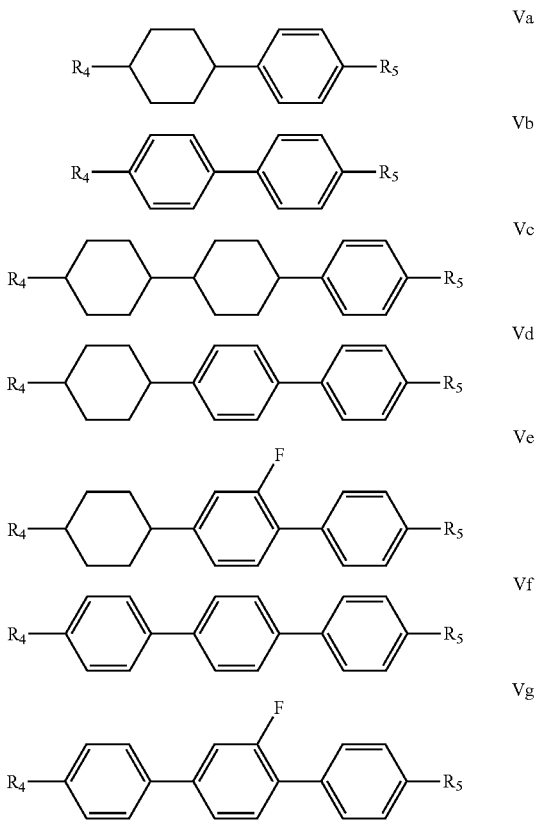

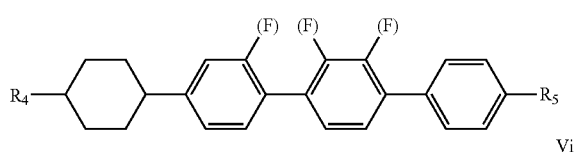

Vh

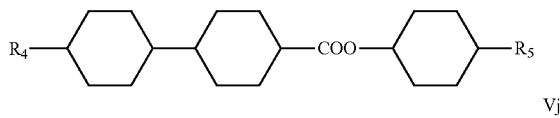

Vi

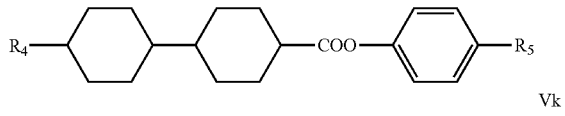

Vj

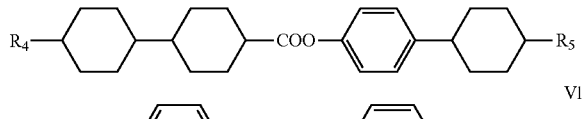

Vk

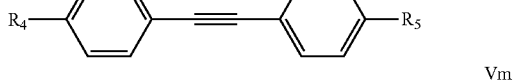

Vl

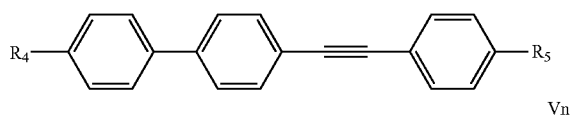

Vm

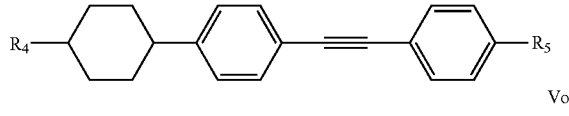

Vn

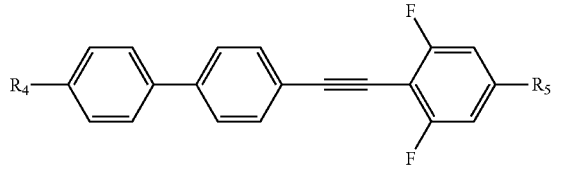

Vo

Vp wherein $R_4$ and $R_5$ each independently represent an alkyl group having 1-10 carbon atoms or an alkenyl group having 2-10 carbon atoms; in addition, any —$CH_2$— of these groups may be replaced with —$CH_2O$—, —$OCH_2$— or —C≡C—, and any hydrogen may be replaced with F; and (F) each independently represents F or H.

Use of the above-mentioned compounds as represented by formula I provided by the present invention in the preparation of a liquid crystal mixture, a liquid crystal display device material or an electro-optical display device material and a liquid crystal mixture, a liquid crystal display device material or an electro-optical display device material that comprises a compound of formula I also fall within the scope of protection of the present invention.

Due to the presence of the rigid structure and the two side fluorines in the molecule, dibenzofuran-based crystals exhibit greater negative dielectric constants, and the presence of the rigid structure also results in a poorer solubility of such compounds, which limits the use thereof. Surprisingly, when a cycloalkyl group is introduced into the dibenzofuran liquid crystal molecule, the resulting liquid crystal compound exhibits a better intersolubility than this type of liquid crystal compounds traditionally having flexible alkyl chains as terminal groups, and thus the use of a compound as represented by formula I provided by the present invention can improve the intersolubility of a liquid crystal compound and extend the application range of a liquid crystal mixture, producing an important application value.

BRIEF DESCRIPTION OF THE DRAWINGS

The FIGURE is a mass spectrum of the compound as represented by formula I12-1.

DETAILED DESCRIPTION OF EMBODIMENTS

The present invention is further described in conjunction with particular examples below, and the present invention is not limited to the following examples. Said methods are all conventional methods, unless otherwise specified. Said raw materials, unless otherwise specified, are commercially available. In the following examples, GC represents a gas chromatographic purity, MP represents a melting point, CP represents a clearing point, MS represents mass spectrum, Δε represents dielectric anisotropy, and Δn represents optical anisotropy. Methods for the determination of GC, MP, CP, MS, Δε and Δn are all conventional methods.

Example 1. Compound as Represented by Formula I1-1

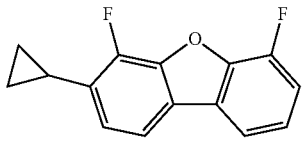 [SMILES: Fc1cccc2c1oc1c(F)c(C3CC3)ccc12]

Step 1

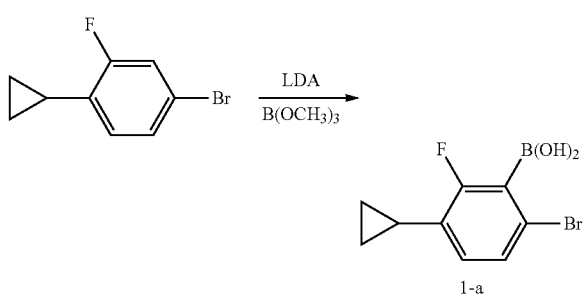

45 g (0.21 mol) of 2-fluoro-4-bromocyclopropylbenzene and 150 mL of tetrahydrofuran are added into a 1 L three-necked flask, stirring is started, nitrogen is charged to replace air, the flask is placed in a cryostat and cooled with liquid nitrogen, when the temperature is decreased to −78° C., 200 ml (0.23 mol) of a solution of 2.5 M diisopropylamine lithium petroleum ether solution is added dropwise within half an hour, and after the reaction proceeds for half an hour, 25 ml of a solution of 27 g (0.25 mol) of trimethyl borate in tetrahydrofuran is further added dropwise at −78°

C. within half an hour to obtain a transparent solution, the cryostat is removed, when the temperature rises spontaneously to −20° C. (for 2 hours), the solution is poured into 750 ml of deionized water having 100 ml of hydrochloric acid for hydrolysis and subjected to liquid separation, the aqueous phase is extracted once with 500 ml of ethyl acetate, and the organic layer is combined and washed to neutral. The solvent is evaporated off under a reduced pressure, 150 ml of petroleum ether is added, and after heating to boiling, cooling and filtration, 45 g of a white solid (1-a) with a yield of 83% is obtained.

Step 2

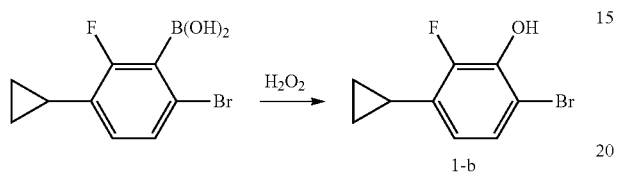

45 g (0.17 mol) of (1-a) and 300 ml of tetrahydrofuran are added to a 1 L three-necked flask and stirred to completely dissolved, and 60 g of hydrogen peroxide is added, stirred uniformly and heated to reflux for 7 h; and the reaction is stopped, the solution is cooled to room temperature, 300 ml of dichloromethane is added, oscillation is carried out for liquid separation, the aqueous layer is extracted with 300 ml×2 of dichloromethane, and the dichloromethane is combined and washed with 300 ml×2 of an aqueous saturated sodium chloride solution, followed by drying with 25 g of anhydrous sodium sulfate and solution rotary drying, to obtain 35 g of a light yellow liquid with a GC of 94.2% and a yield of 88%.

Step 3

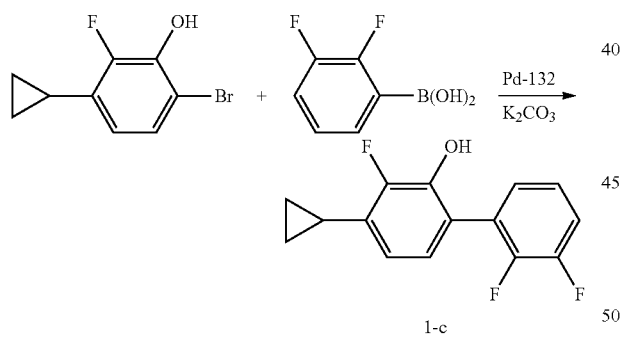

33 g (0.14 mol) of (1-b), 22.6 (0.14 mol) of 2,3-difluorobenzene boric acid, 43 g (0.31 mol) of potassium carbonate, 300 ml of toluene and 100 ml of pure water are added to a 1 L three-necked flask and stirred to completely dissolved, 0.05 g of Pd-132 is added under the protection of nitrogen, followed by heating and a reflux reaction for 5 h; and the reaction is stopped, 300 ml of pure water is added and stirred for liquid separation, the aqueous layer is extracted with 200 ml×2 of toluene, the organic layer is combined and washed with 300 ml×2 of saturated salt solution, followed by the rotary drying of the solvent under a reduced pressure, 100 g of petroleum ether is added to the resulting liquid and stirred uniformly, and recrystallization is carried out at −20° C. to obtain 30 g of a white solid (1-c) with a GC of 99.0% and a yield of 81%.

Step 4

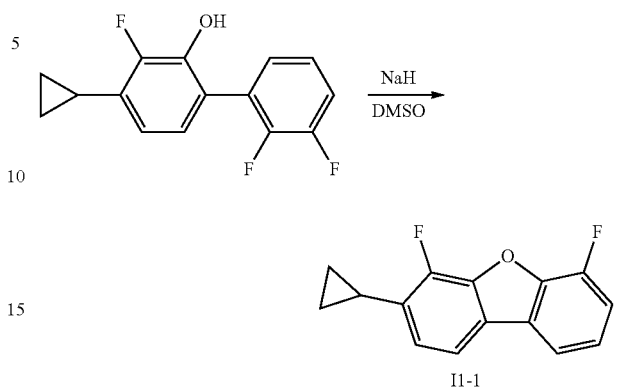

30 g (0.11 mol) of (1-c) is added to a 500 ml three-necked flask, 200 ml of dimethylsulfoxide (DMSO) is added under the protection of nitrogen and stirred uniformly, and 8.8 g (0.22 mol) of 60% sodium hydride mineral oil is added, heated to 120° C. and stirred for 4 hours; and the reaction is stopped, the reaction liquid is cooled to room temperature, poured to 300 g of ice water and stirred, a large amount of solid is precipitated, the solid is subjected to suction filtration with a filter cloth and aired to obtain a solid, 200 ml of petroleum ether is added and heated to complete dissolution, followed by passing through a 30 g hot silica gel column, the column is rinsed with 200 ml of hot petroleum ether, and after the rotary drying of the solution, 1 fold of toluene and 2 folds of petroleum ether are added and heated to complete dissolution, followed by recrystallization at 0° C. twice, to obtain 12 g of a white solid (I1-1) with a GC of 99.90% and a yield of 42%.

Example 2. Compound as Represented by Formula I5-1

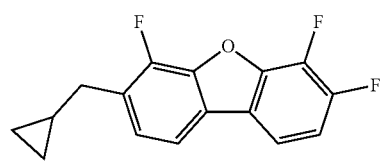 [SMILES: Fc1ccc2c(oc3c(F)c(CC4CC4)ccc32)c1F]

Step 1

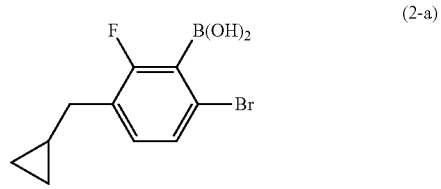 [SMILES: OB(O)c1c(Br)ccc(CC2CC2)c1F]

is synthesized using 2-fluoro-4-bromocyclopropylbenzene as a raw material with reference to Step 1 in Example 1;

Step 2

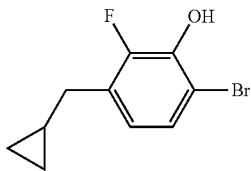
(2-b)

is synthesized using (2-a) as a raw material with reference to Step 2 in Example 1;
Step 3

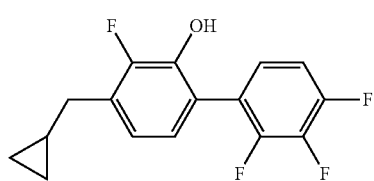
(2-c)

is synthesized using (2-b) and 2,3,4-trifluorobenzeneboronic acid as raw materials with reference to Step 3 in Example 1; and
Step 4
the target compound I5-1

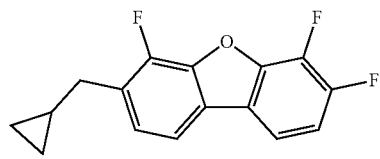 [SMILES: Fc1ccc2c(oc3c(F)c(CC4CC4)ccc32)c1F]

is synthesized using (2-c) as a raw material with reference to Step 4 in Example 1.

Example 3. Compound as Represented by Formula I9-1

Step 1

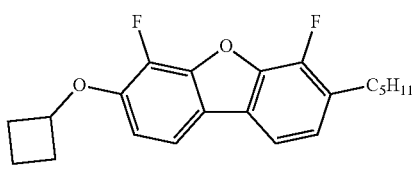

Step 2

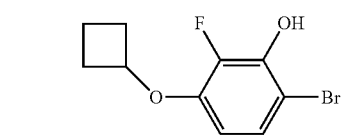
(3-b)

is synthesized using (3-a) as a raw material with reference to Step 2 in Example 1;
Step 3

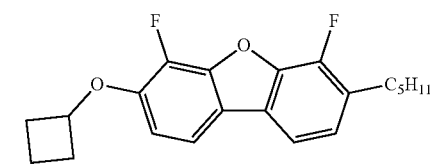
(3-c)

is synthesized using (3-b) and 2,3-difluoro-4-pentylbenzeneboronic acid as raw materials with reference to Step 3 in Example 1; and
Step 4
the target compound I9-1

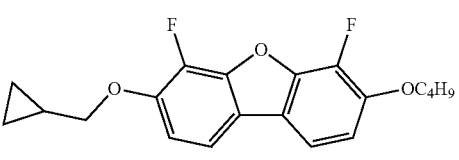

is synthesized using (3-c) as a raw material with reference to Step 4 in Example 1.

Example 4. Compound as Represented by Formula I12-1

Step 1

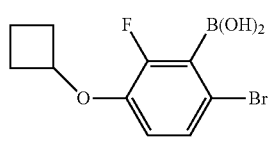
(3-a)

is synthesized using 2-fluoro-4-bromobenzenecyclobutyl ether as a raw material with reference to Step 1 in Example 1;

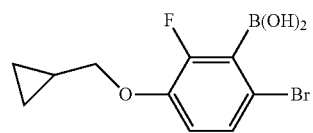
(4-a)

is synthesized using 2-fluoro-4-bromobenzenecyclopropyl methyl ether as a raw material with reference to Step 1 in Example 1;

Step 2

(4-b)

is synthesized using (4-a) as a raw material with reference to Step 2 in Example 1;

Step 3

(4-c)

is synthesized using (4-b) and 2,3-difluoro-4-butoxybenzeneboronic acid as raw materials with reference to Step 3 in Example 1; and Step 4 the target compound I12-1 is synthesized using (4-c) as a raw material with reference to Step 4 in Example 1.

Example 5. Compound as Represented by Formula I15-2

Step 1

(5-a)

is synthesized using 2-(2-fluoro-4-bromophenethyl)tetrahydrofuran as a raw material with reference to Step 1 in Example 1;

Step 2

(5-b)

is synthesized using (5-a) as a raw material with reference to Step 2 in Example 1;

Step 3

(5-c)

is synthesized using (5-b) and 2,3-difluoro-4-butoxybenzeneboronic acid as raw materials with reference to Step 3 in Example 1; and Step 4 the target compound I15-2 is synthesized using (5-c) as a raw material with reference to Step 4 in Example 1.

Example 6. Compound as Represented by Formula I12-2

Step 1

(6-a)

is synthesized using 2-fluoro-4-bromobenzenecyclopentyl methyl ether as a raw material with reference to Step 1 in Example 1;

Step 2

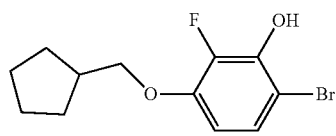
(6-b)

is synthesized using (6-a) as a raw material with reference to Step 2 in Example 1;

Step 3

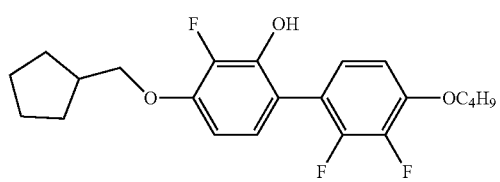
(6-c)

is synthesized using (6-b) and 2,3-difluoro-4-butoxybenzeneboronic acid as raw materials with reference to Step 3 in Example 1; and Step 4 the target compound I12-2

is synthesized using (6-c) as a raw material with reference to Step 4 in Example 1.

Mixture Examples

In the following examples, the parts involved therein are all in weight percentage content, the temperature unit is ° C., and the specific meaning of the other symbols and the test conditions are as follows:

S—N represents the melting point (° C.) of the liquid crystal from a crystal state to a nematic phase;

c.p. represents the clear point (° C.) of a liquid crystal, with the test instrument being Mettler-Toledo-FP System microthermal analyzer;

γ1 is rotary viscosity (mPa·s), with the test conditions being: 25° C., INSTEC: ALCT-IR1, and a 18 micron vertical box;

$K_{11}$ is a twist elastic constant, and $K_{33}$ is a splay elasticity constant, with the test conditions being: 25° C., INSTEC: ALCT-IR1 and a 18 micron vertical box;

Δε represents dielectric anisotropy, $\Delta\varepsilon=\varepsilon//-\varepsilon_\perp$, wherein ε// is the dielectric constant parallel to the molecular axis, and $\varepsilon_\perp$ is the dielectric constant perpendicular to the molecular axis, with the test conditions being: 25° C., INSTEC: ALCT-IR1 and an 18 micron vertical box;

Δn represents optical anisotropy, $\Delta n = n_o - n_e$, wherein $n_o$ is the refractive index of an ordinary light, $n_e$ is the refractive index of an extraordinary light, with the test conditions being: 589 nm, 25±0.2° C.;

In the following Examples 1 to 11, liquid crystal compounds of general formulas I, II, III and IV are weighed separately in a ratio to prepare liquid crystal media. All the various liquid crystal monomers used may be synthesized by known methods or be commercially available.

Devices and instruments used to prepare the liquid crystal media are:

(1) an electronic precision balance (with an accuracy of 0.1 mg)

(2) stainless steel beakers for liquid crystal weighing (3) spoons for monomer addition (4) a magnetic rotor for stirring (5) a temperature-controlled electromagnetic stirrer The method for preparing a liquid crystal medium comprises the following steps:

(1) monomers to be used are placed in order neatly;

(2) a stainless steel beaker is placed on the balance, and the monomers are placed into the stainless steel beaker with small spoons;

(3) monomer liquid crystals are added in sequence in weights as required;

(4) the stainless steel beaker with the materials having been added is placed on the magnetic stirrer, heated and melted; and (5) after most of the mixture in the stainless steel beaker is melted, a magnetic rotor is added to the stainless steel beaker to stir the liquid crystal mixture uniformly, and the mixture is cooled to room temperature to obtain the liquid crystal medium.

The obtained liquid crystal medium is filled between two substrates of a liquid crystal display for performance test. The test results of the monomer structures of the specific compounds, the amounts (in weight percentage content), and the performance parameters of the resulting liquid crystal medium are listed in tables.

TABLE 1

The ratio of the components of the liquid crystal composition of Example 6 and the performance parameters thereof

| Compound General formula | Liquid crystal structure formula | Weight percentage content (%) | Performance parameter |
|---|---|---|---|
| V | C₃H₇—⟨⟩—⟨⟩—OC₂H₅ | 3 | S-N: ≤−40° C. c.p: 90° C. γ₁: 125 mPa·s Δn: 0.108 |
| V | C₃H₇—⟨⟩—⟨⟩—C₅H₁₁ | 10 | $n_e$: 1.596 Δε: −4.0 $\varepsilon_\perp$: 8.0 $K_{11}/K_{33}$: 14.5/15.7 |

TABLE 1-continued

The ratio of the components of the liquid crystal composition of Example 6 and the performance parameters thereof

| Compound General formula | Liquid crystal structure formula | Weight percentage content (%) | Performance parameter |
|---|---|---|---|
| V | C$_3$H$_7$—⬡—⬡—C$_2$H$_5$ | 10 | After the composition is stored at −20° C. for 480 h, no crystallization occurs. |
| V | C$_2$H$_5$—⬡—⬡—⬢—C$_3$H$_7$ | 10 | |
| IV | (propyl)—⬡—⬢(F,F)—OC$_2$H$_5$ | 9 | |
| IV | (propyl)—⬡—⬢(F,F)—OC$_4$H$_9$ | 9 | |
| IV | C$_2$H$_5$—⬡—⬡—⬢(F,F)—CH$_3$ | 8 | |
| IV | C$_3$H$_7$—⬡—⬡—⬢(F,F)—CH$_3$ | 4 | |
| IV | C$_3$H$_7$—⬡—⬡—⬢(F,F)—OC$_2$H$_5$ | 3 | |
| IV | C$_2$H$_5$—⬡—⬡—⬢(F,F)—OC$_2$H$_5$ | 5 | |
| IV | C$_4$H$_9$—⬡—⬢—naphthyl(F,F,F,F)—OC$_2$H$_5$ | 5 | |
| IV | C$_2$H$_5$—⬡—⬢—⬢(F,F)—OC$_2$H$_5$ | 6 | |
| IV | C$_3$H$_7$—⬡—⬢(F,F)—C$_2$H$_4$—⬢(F,F)—OC$_2$H$_5$ | 2 | |

TABLE 1-continued

The ratio of the components of the liquid crystal composition of
Example 6 and the performance parameters thereof

| Compound General formula | Liquid crystal structure formula | Weight percentage content (%) | Performance parameter |
|---|---|---|---|
| I | [structure: dibenzofuran with F, F, O-cyclobutylmethyl, OC_5H_11] | 9 | |
| I | [structure: dibenzofuran with F, F, O-cyclopentylmethyl, OC_4H_9] | 7 | |

TABLE 2

The ratio of the components of the liquid crystal composition of
Example 7 and the performance parameters thereof

| Compound General formula | Liquid crystal structure formula | Weight percentage content (%) | Performance parameter |
|---|---|---|---|
| V | $C_3H_7$—[Cy]—[Cy]—CH=CH$_2$ | 38 | S-N: ≤−40° C. c.p: 98° C. $\gamma_1$: 147 mPa·s $\Delta n$: 0.113 |
| V | CH$_2$=CH—[Cy]—[Cy]—[Ph]—CH$_3$ | 3 | $n_e$: 1.612 $\Delta\varepsilon$: −6.1 $\varepsilon_\perp$: 110 $K_{11}/K_{33}$: 14.7/16.3 |
| IV | [C_3H_7-Cy]—CH$_2$O—[Ph(F,F)]—OC$_2$H$_5$ | 5 | After the composition is stored at −20° C. for 480 h, no crystallization occurs. |
| IV | [C_4H_9-Cy]—CH$_2$O—[Ph(F,F)]—OC$_2$H$_5$ | 8 | Low temperature intersolubility indicator? |
| IV | [C_3H_7-Cy-Cy]—CH$_2$O—[Ph(F,F)]—OC$_2$H$_5$ | 5 | |
| IV | [C_2H_5-Cy-Cy]—CH$_2$O—[Ph(F,F)]—OC$_2$H$_5$ | 5 | |
| IV | $C_3H_7$—[Cy]—[Ph]—[Ph(F,F)]—OC$_2$H$_5$ | 6 | |

TABLE 2-continued

The ratio of the components of the liquid crystal composition of Example 7 and the performance parameters thereof

| Compound General formula | Liquid crystal structure formula | Weight percentage content (%) | Performance parameter |
|---|---|---|---|
| IV | $C_5H_{11}$—[phenyl]—[phenyl]—[2,3-difluoro-phenyl]—$OC_2H_5$ | 6 | |
| I | cyclopropylmethyl-substituted tetrafluorodibenzofuran (F at 1,4,6-positions; three F shown) | 8 | |
| I | cyclopropyl-substituted difluorodibenzofuran (F at 4,6-positions) | 16 | |

TABLE 3

The ratio of the components of the liquid crystal composition of Example 8 and the performance parameters thereof

| Compound General formula | Liquid crystal structure formula | Weight percentage content (%) | Performance parameter |
|---|---|---|---|
| V | $C_3H_7$—[Cy]—[Cy]—$C_2H_5$ | 12 | S-N: ≤−40° C. |
| V | $C_3H_7$—[Cy]—[Cy]—$C_2H_{11}$ | 10 | c.p: 97° C. |
| V | $C_3H_7$—[Cy]—[Cy]—[Ph]—$C_3H_7$ | 3 | $\gamma_1$: 174 mPa·s |
| | | | $\Delta n$: 0.144 |
| | | | $n_e$: 1.632 |
| | | | $\Delta\varepsilon$: −5.0 |
| | | | $\varepsilon_\perp$: 8.5 |
| | | | $K_{11}/K_{33}$: 15.2/17.0 |
| | | | After the composition is stored at −20° C. for 480 h, no crystallization occurs. |
| V | $C_3H_7$—[Cy]—[Ph]—C≡C—[Ph]—$C_5H_{11}$ | 5 | |
| IV | ethyl—[Cy]—[2,3-difluorophenyl]—C≡C—[2,3-difluorophenyl]—$OC_2H_5$ | 3 | |
| IV | $C_5H_{11}$—[Cy]—[Cy]—[2,3-difluorophenyl]—$OC_2H_5$ | 9 | |

TABLE 3-continued

The ratio of the components of the liquid crystal composition of
Example 8 and the performance parameters thereof

| Compound General formula | Liquid crystal structure formula | Weight percentage content (%) | Performance parameter |
|---|---|---|---|
| IV | C5H7–[Cy]–[Ph]–[Ph(2,3-F)]–OC2H5 | 6 | |
| IV | C5H11–[Ph]–[Ph]–[Ph(2,3-F)]–OC2H5 | 3 | |
| IV | C5H11–[Ph]–[Ph]–[Ph(2,3-F)]–OC2H5 | 5 | |
| IV | C3H7–[Ph]–C≡C–[Ph(2,3-F)]–OC2H5 | 15 | |
| IV | C3H7–[Ph(2,3-F)]–C≡C–[Ph(2,3-F)]–OC2H5 | 13 | |
| I | cyclobutyl-O–[dibenzofuran(F,F)]–C5H11 | 6 | |
| I | cyclopropyl–[dibenzofuran(F,F)] | 10 | |

TABLE 4

The ratio of the components of the liquid crystal composition of
Example 9 and the performance parameters thereof

| Compound General formula | Liquid crystal structure formula | Weight percentage content (%) | Performance parameter |
|---|---|---|---|
| V | C3H7–[Cy]–[Cy]–CH=CH2 | 17 | S-N: ≤−40° C.<br>c.p: 105° C.<br>$\gamma_1$: 175 mPa·s<br>$\Delta n$: 0.130<br>$n_e$: 1.575<br>$\Delta\varepsilon$: −4.6<br>$\varepsilon_\perp$: 8.6<br>$K_{11}/K_{33}$: 15.5/17.0 |
| V | CH2=CH–[Cy]–[Cy]–[Ph]–CH3 | 12 | |

TABLE 4-continued

The ratio of the components of the liquid crystal composition of
Example 9 and the performance parameters thereof

| Compound General formula | Liquid crystal structure formula | Weight percentage content (%) | Performance parameter |
|---|---|---|---|
| V | C₃H₇—⟨cyclohexyl⟩—⟨phenyl⟩—⟨phenyl⟩—C₃H₇ | 4 | After the composition is stored at −20° C. for 480 h, no crystallization occurs. |
| V | C₃H₇—⟨cyclohexyl⟩—⟨cyclohexyl⟩—COO—⟨phenyl⟩—C₃H₇ | 3 | |
| V | C₃H₇—⟨cyclohexyl⟩—⟨cyclohexyl⟩—COO—⟨phenyl⟩—⟨cyclohexyl⟩—C₃H₇ | 5 | |
| IV | C₃H₇—⟨cyclohexyl⟩—⟨cyclohexyl⟩—⟨phenyl(F,F)⟩—OC₂H₅ | 5 | |
| IV | C₃H₇—⟨cyclohexyl⟩—⟨cyclohexyl⟩—COO—⟨phenyl(F,F)⟩—OC₂H₅ | 4 | |
| IV | C₃H₁₁—⟨cyclohexyl⟩—⟨cyclohexyl⟩—COO—⟨phenyl(F,F)⟩—OC₂H₅ | 4 | |
| IV | C₃H₇—⟨cyclohexyl⟩—⟨phenyl⟩—⟨naphthyl(F,F,F)⟩—OC₄H₉ | 8 | |
| IV | C₂H₅—⟨cyclohexyl⟩—⟨phenyl⟩—⟨phenyl(F,F)⟩—OC₂H₅ | 8 | |
| IV | C₂H₅—⟨phenyl⟩—⟨phenyl(F,F)⟩—⟨phenyl⟩—C₃H₇ | 5 | |
| IV | C₃H₇—⟨cyclohexyl⟩—⟨naphthyl(F,F,F)⟩—OC₂H₅ | 12 | |

TABLE 4-continued

The ratio of the components of the liquid crystal composition of
Example 9 and the performance parameters thereof

| Compound General formula | Liquid crystal structure formula | Weight percentage content (%) | Performance parameter |
|---|---|---|---|
| IV | 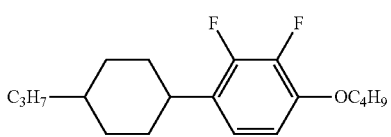 | 12 | |
| I | 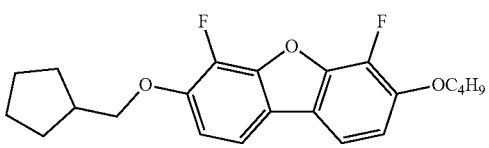 | 1 | |

TABLE 5

The ratio of the components of the liquid crystal composition of
Example 10 and the performance parameters thereof

| Compound General formula | Liquid crystal structure formula | Weight percentage content (%) | Performance parameter |
|---|---|---|---|
| V | 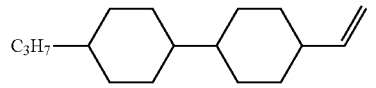 | 14 | S-N: ≤−40° C. c.p: 106° C. $\gamma_1$: 166 Pa•s Δn: 0.106 |
| V |  | 7 | $n_e$: 1.595 Δε: −5.7 $\varepsilon_\perp$: 8.8 $K_{11}/K_{33}$: 14.2/16.0 |
| V |  | 3 | After the composition is stored at −20° C. for 480 h, no crystallization occurs. |
| V | 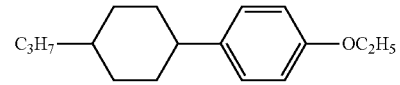 | 8 | |
| V | 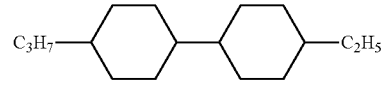 | 7 | |
| V | 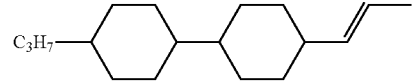 | 7 | |
| IV | 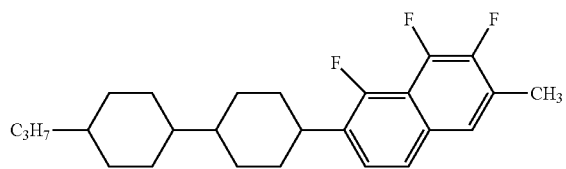 | 5 | |
| IV | 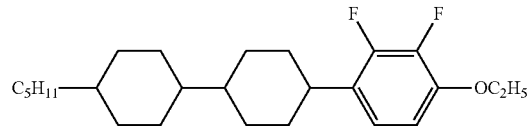 | 5 | |

TABLE 5-continued

The ratio of the components of the liquid crystal composition of
Example 10 and the performance parameters thereof

| Compound General formula | Liquid crystal structure formula | Weight percentage content (%) | Performance parameter |
|---|---|---|---|
| IV | 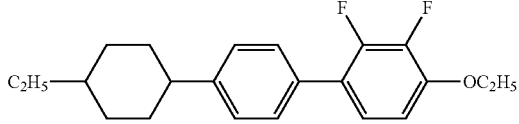 [SMILES: CCOc1ccc(-c2ccc(C3CCC(CC)CC3)cc2)c(F)c1F] | 4 | |
| IV | 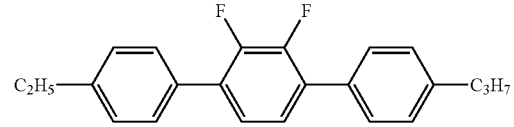 | 5 | |
| IV | 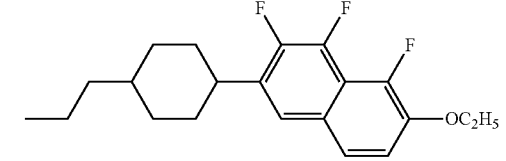 [SMILES: CCCC1CCC(c2cc3ccc(OCC)c(F)c3c(F)c2F)CC1] | 10 | |
| IV | 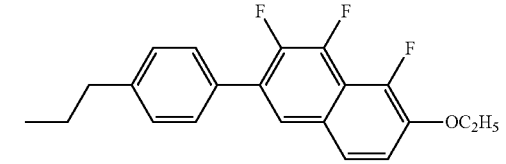 [SMILES: CCCc1ccc(-c2cc3ccc(OCC)c(F)c3c(F)c2F)cc1] | 10 | |
| IV | 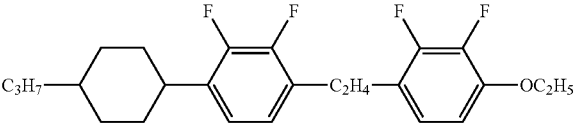 | 5 | |
| I | 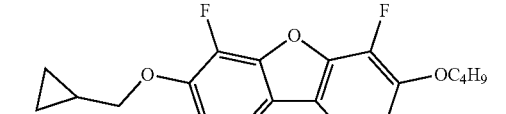 | 5 | |

TABLE 6

The ratio of the components of the liquid crystal composition of
Example 11 and the performance parameters thereof

| Compound General formula | Liquid crystal structure formula | Weight percentage content (%) | Performance parameter |
|---|---|---|---|
| V | 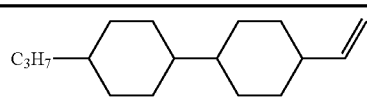 | 32 | S-N: ≤−40° C. c.p: 95° C. $\gamma_1$: 115 mPa•s $\Delta n$: 0.122 |
| IV | 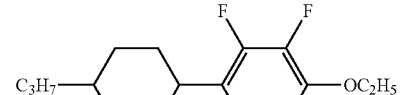 | 12 | $n_e$: 1.603 $\Delta\varepsilon$: −5.5 $\varepsilon_\perp$: 9.0 $K_{11}/K_3$: 14.5/16.5 After the composition is |
| IV | 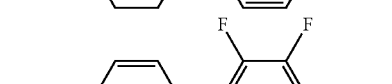 | 12 | stored at −20° C. for 480 h, no crystallization occurs. |

TABLE 6-continued

The ratio of the components of the liquid crystal composition of
Example 11 and the performance parameters thereof

| Compound General formula | Liquid crystal structure formula | Weight percentage content (%) | Performance parameter |
|---|---|---|---|
| IV | 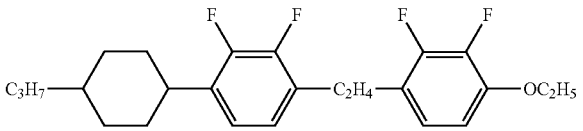 | 8 | |
| IV | 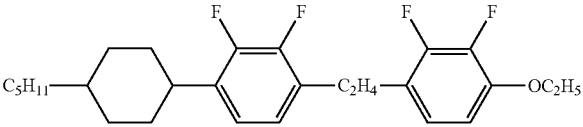 | 8 | |
| IV | 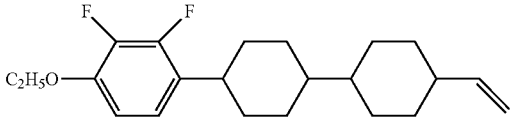 | 8 | |
| IV | 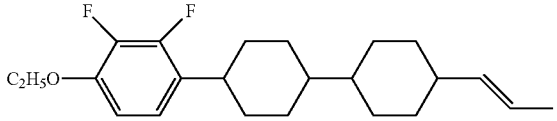 | 8 | |
| I | 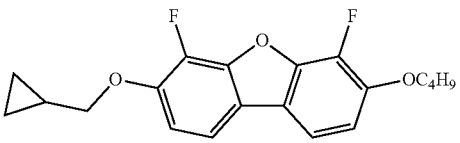 | 5 | |
| I | 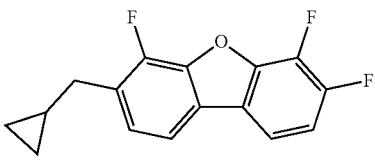 [SMILES: Fc1ccc2c(oc3c(F)c(CC4CC4)ccc32)c1F] | 7 | |

TABLE 7

The ratio of the components of the liquid crystal composition of
Example 12 and the performance parameters thereof

| Compound General formula | Liquid crystal structure formula | Weight percentage content (%) | Performance parameter |
|---|---|---|---|
| V | 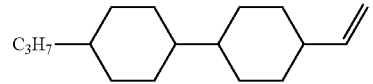 | 38 | S-N: ≤−40° C. c.p: 100° C. $\gamma_1$: 148 mPa·s $\Delta n$: 0.115 |
| V | 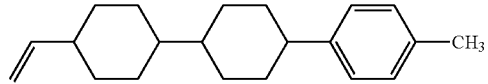 [SMILES: C=CC1CCC(C2CCC(c3ccc(C)cc3)CC2)CC1] | 3 | $n_e$: 1.617 $\Delta\varepsilon$: −6.0 $\varepsilon_\perp$: 11.0 $K_{11}/K_{33}$: 14.8/16.6 |
| IV | 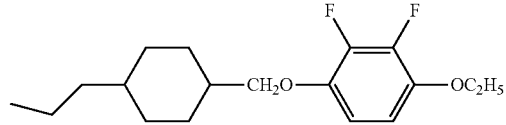 | 5 | After the composition is stored at −20° C. for 480 h, no crystallization occurs. |

TABLE 7-continued

The ratio of the components of the liquid crystal composition of Example 12 and the performance parameters thereof

| Compound General formula | Liquid crystal structure formula | Weight percentage content (%) | Performance parameter |
|---|---|---|---|
| IV | [structure: propyl-cyclohexyl-CH₂O-difluorophenyl-OC₂H₅] | 8 | Is there any data under the conditions of −20° C.? |
| IV | [structure: propyl-cyclohexyl-cyclohexyl-CH₂O-difluorophenyl-OC₂H₅] | 10 | |
| IV | [structure: ethyl-cyclohexyl-cyclohexyl-CH₂O-difluorophenyl-OC₂H₅] | 10 | |
| IV | [structure: C₃H₇-cyclohexyl-phenyl-difluorophenyl-OC₂H₅] | 6 | |
| IV | [structure: C₅H₁₁-phenyl-phenyl-difluorophenyl-OC₂H₅] | 6 | |
| I | [structure: cyclopropyl-difluorodibenzofuran] | 9 | |
| I | [structure: tetrahydrofuranyl-ethyl-difluorodibenzofuran-OC₄H₉] | 5 | |

TABLE 8

The ratio of the components of the liquid crystal composition of Example 13 and the performance parameters thereof

| Compound General formula | Liquid crystal structure formula | Weight percentage content (%) | Performance parameter |
|---|---|---|---|
| V | [structure: C₃H₇-cyclohexyl-cyclohexyl-vinyl] | 14 | S-N: ≤−20° C. c.p: 105° C. $\gamma_1$: 123 Pa•s $\Delta n$: 0.105 |
| V | [structure: vinyl-cyclohexyl-cyclohexyl-phenyl-CH₃] | 7 | $n_e$: 1.594 $\Delta\varepsilon$: −5.4 $\varepsilon_\perp$: 8.5 $K_{11}/K_{33}$: 13.3/15.0 |

TABLE 8-continued
The ratio of the components of the liquid crystal composition of Example 13 and the performance parameters thereof
| Compound General formula | Liquid crystal structure formula | Weight percentage content (%) | Performance parameter |
|---|---|---|---|
| V |  | 3 | After the composition is stored at −20° C. for 240 h, no crystallization occurs. |
| V | 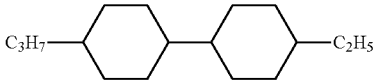 | 8 | |
| V | 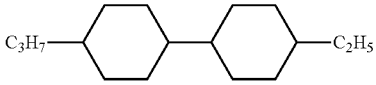 | 7 | |
| V | 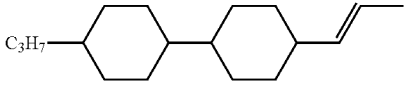 | 7 | |
| IV | 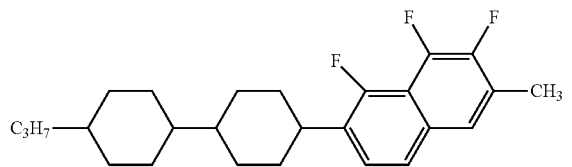 | 5 | |
| IV | 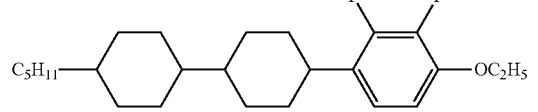 | 5 | |
| IV | 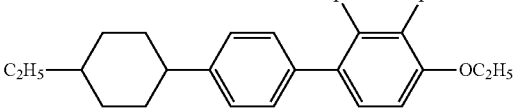 | 4 | |
| IV | 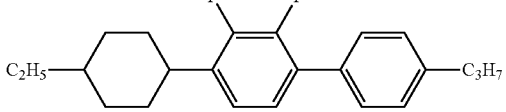 | 5 | |
| IV | 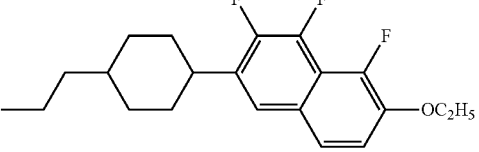 | 10 | |
| IV | 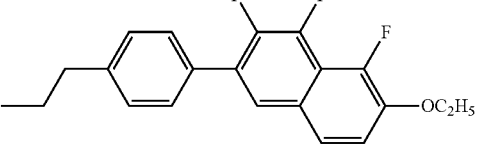 | 10 | |
| IV | 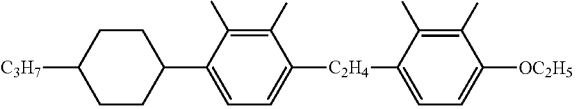 | 5 | |

TABLE 8-continued

The ratio of the components of the liquid crystal composition of
Example 13 and the performance parameters thereof

| Compound General formula | Liquid crystal structure formula | Weight percentage content (%) | Performance parameter |
|---|---|---|---|
| I | C₅H₁₁O—[dibenzofuran with F,F]—OC₄H₉ | 5 | |

As can be seen from the performance parameters of the liquid crystal compositions shown in Examples 6-12, the liquid crystal compositions of the present invention have a very good intersolubility and a very great negative dielectric constant; moreover, as can be seen upon the comparison between Example 10 and Example 13, the dibenzofuran-based liquid crystal compound having the cycloalkyl as the terminal group, compared with the dibenzofuran-based liquid crystal having the traditional flexible alkyl chain as the terminal group, exhibits a better intersolubility, and thus the use of a compound as represented by formula i provided by the present invention can improve the intersolubility of a liquid crystal compound and extend the application range of a liquid crystal mixture, producing an important application value.

Although only the specific compounds of the above-mentioned 8 examples and the compounding amounts (weight percentage content) thereof are listed and subjected to a performance test in the present invention, the liquid crystal compositions of the present invention can be further expanded and modified on the basis of the above-mentioned examples using the liquid crystal compounds represented by general formulas I, IV and V and the preferred liquid crystal compounds of general formulas I, IV and V, and they can all achieve the object of the present invention by appropriately adjusting the ratio thereof.

The invention claimed is:

1. Compounds as represented by formula I

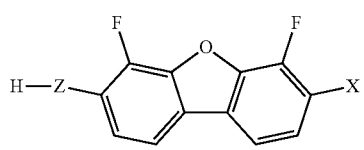

wherein H represents one of cyclopropyl, cyclobutyl, cyclopentyl or 2-tetrahydrofuranyl; Z represents one of a single bond, —CH₂—, —O—, —CH₂CH₂— or —CH₂O—; and X represents a hydrogen atom, a fluorine atom, an alkyl group having 1-7 carbon atoms or an alkoxy group having 1-7 carbon atoms.

2. The compounds according to claim 1, wherein the compounds as represented by said formula I are specifically compounds as represented by formulas I1 to I15:

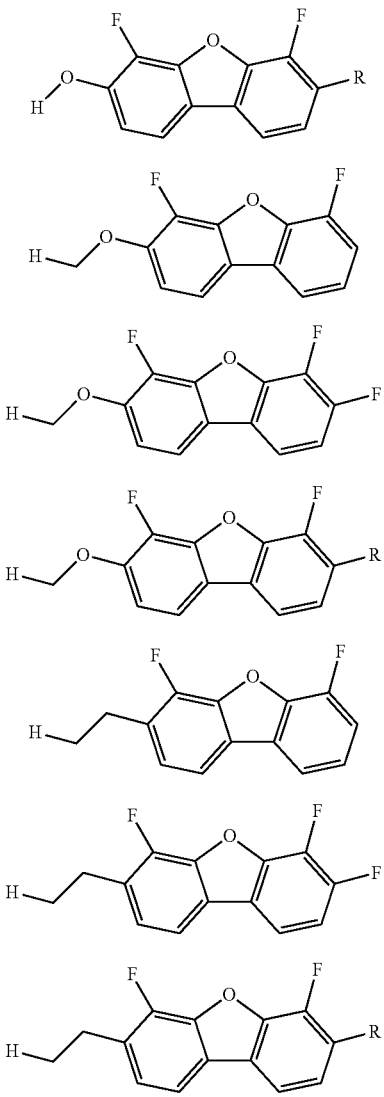

wherein H each independently represents one of cyclopropyl, cyclobutyl or 2-tetrahydrofuranyl; and R each independently represents one of an alkyl group having 1-7 carbon atoms or an alkoxy group having 1-7 carbon atoms.

3. The compounds according to claim 1, wherein the compounds as represented by said formula I are specifically the following compounds as represented by I1-1 to I15-2:

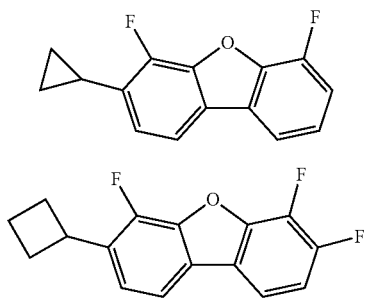

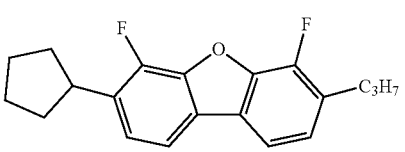
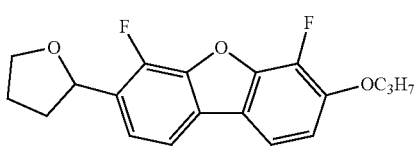
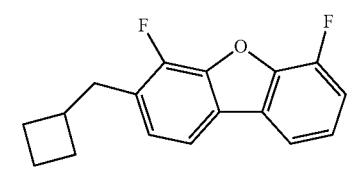
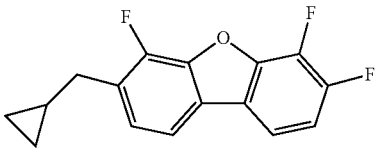
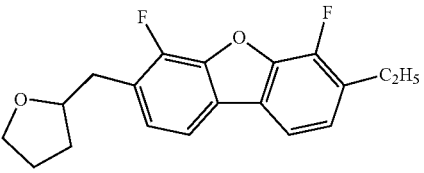
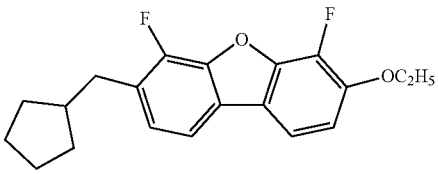
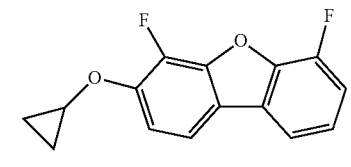
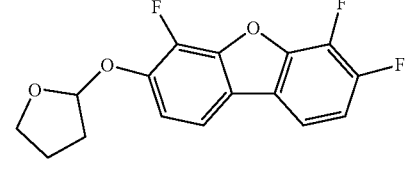
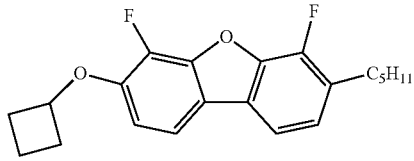

-continued

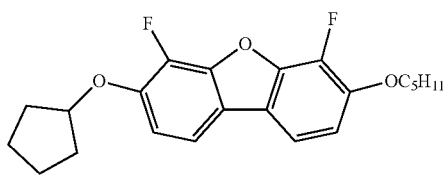
I9-2

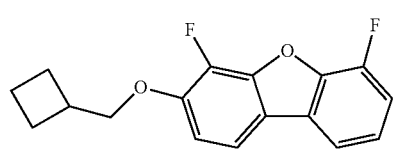
I10-1

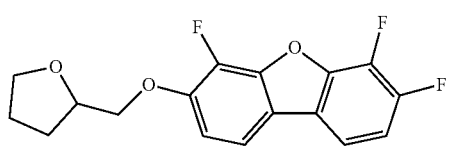
I11-1

-continued

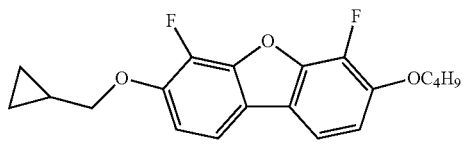
I12-1

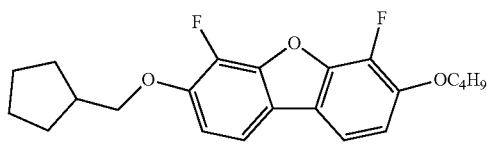
I12-2

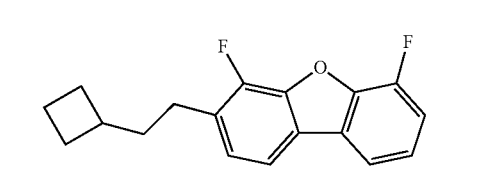
I13-1

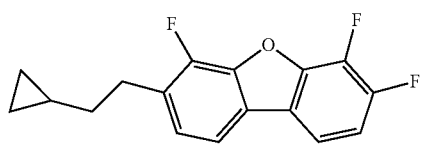
I14-1

-continued

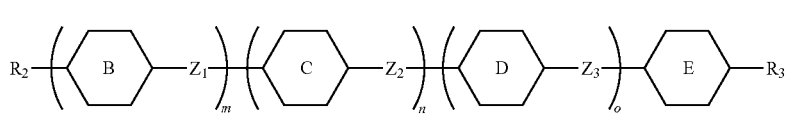
I15-1, I15-2

4. A liquid crystal medium, wherein said liquid crystal medium comprises one or more compounds as represented by formula I in claim 1.

5. The liquid crystal medium according to claim 4, wherein said liquid crystal medium further comprises one or more compounds as represented by formula IV:

$$R_2-\left(\!\!\left(\,B\,\right)\!\!-Z_1\right)_{\!m}\!\!\left(\!\!\left(\,C\,\right)\!\!-Z_2\right)_{\!n}\!\!\left(\!\!\left(\,D\,\right)\!\!-Z_3\right)_{\!o}\!\!\left(\,E\,\right)\!\!-R_3 \qquad \text{IV}$$

in said formula IV, $R_2$ and $R_3$ each independently represent any one of groups as shown by (1) to (3) below:
(1) linear alkyl groups having 1-7 carbon atoms or linear alkoxy groups having 1-7 carbon atoms;
(2) groups formed by substituting one or more —CH$_2$— in any one of the groups as shown by (1) with —O—, —COO—, —OOC— or —CH=CH—; and
(3) groups formed by substituting one or more —H in any one of the groups as represented by (1) with —F, —Cl, —CH=CH$_2$ or —CH=CH—CH$_3$;
rings B, C, D and E each independently represent the following groups:

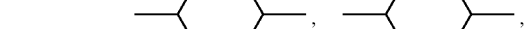

-continued

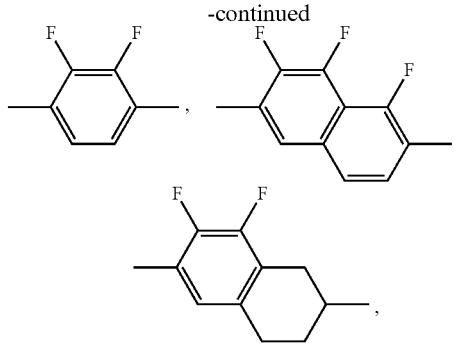, or and at least one of said rings B, C, D and E is selected from

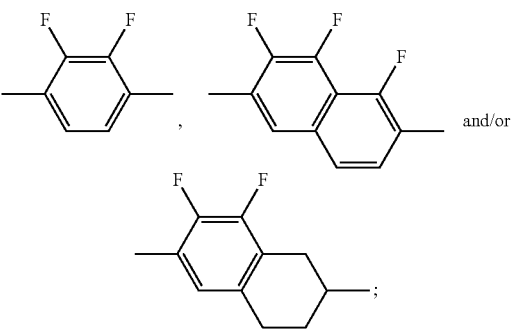 and/or m, n and o each independently represent 0 or 1;

$Z_1$, $Z_2$ and $Z_3$ each independently represent a single bond, —$C_2H_4$—, —CH=CH—, —≡—, —COO—, —OOC—, —$CH_2O$—, —$OCH_2$—, —$CF_2O$— or —$OCF_2$—; wherein additionally, any H atom of these groups may be replaced with F.

6. The liquid crystal medium according to claim 5, wherein said liquid crystal medium further comprises one or more compounds as represented by formula V:

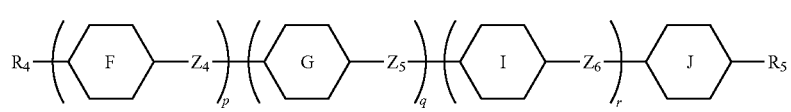

in said formula V, $R_4$ and $R_5$ each independently represent an alkyl group having 1-10 carbon atoms or an alkenyl group having 2-10 carbon atoms; in addition, any —$CH_2$— of these groups may be replaced with —$CH_2O$—, —$OCH_2$— or —C≡C—, and any hydrogen may be replaced with F;

rings F, G, I and J each independently represent the following groups:

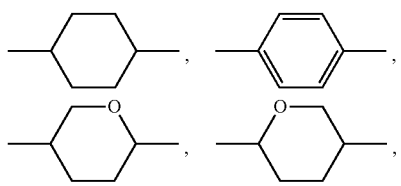

-continued

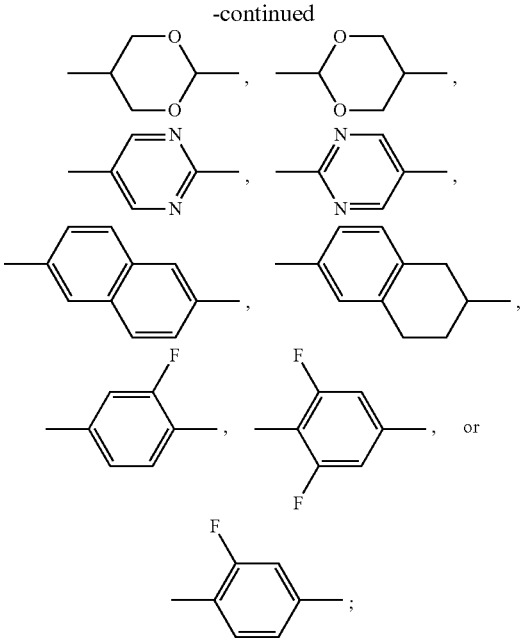

p, q and r each independently represent 0 or 1;

$Z_4$, $Z_5$ and $Z_6$ each independently represent a single bond, —$C_2H_4$—, —CH=CH—, —≡—, —COO—, —OOC—, —$CH_2O$—, —$OCH_2$—, —$CF_2O$—, or —$OCF_2$—; wherein additionally, any H atom of these groups may be replaced with F.

7. The liquid crystal medium according to claim 6, wherein in said liquid crystal medium, the total content in weight percentage of one or more compounds as represented by formula I is 1-24%, the total content in weight percentage of one or more compounds as represented by formula IV is 35-58%, and the total content in weight percentage of one or more compounds as represented by formula V is 30-46%.

8. The liquid crystal medium according to claim 5, wherein said one or more compounds as represented by formula IV are one or more of the compounds as represented by formulas IVa- to IVo:

IVa
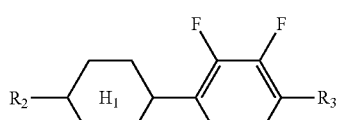

IVb
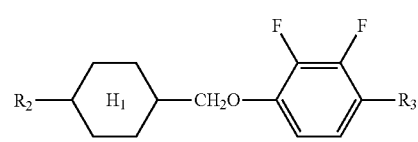

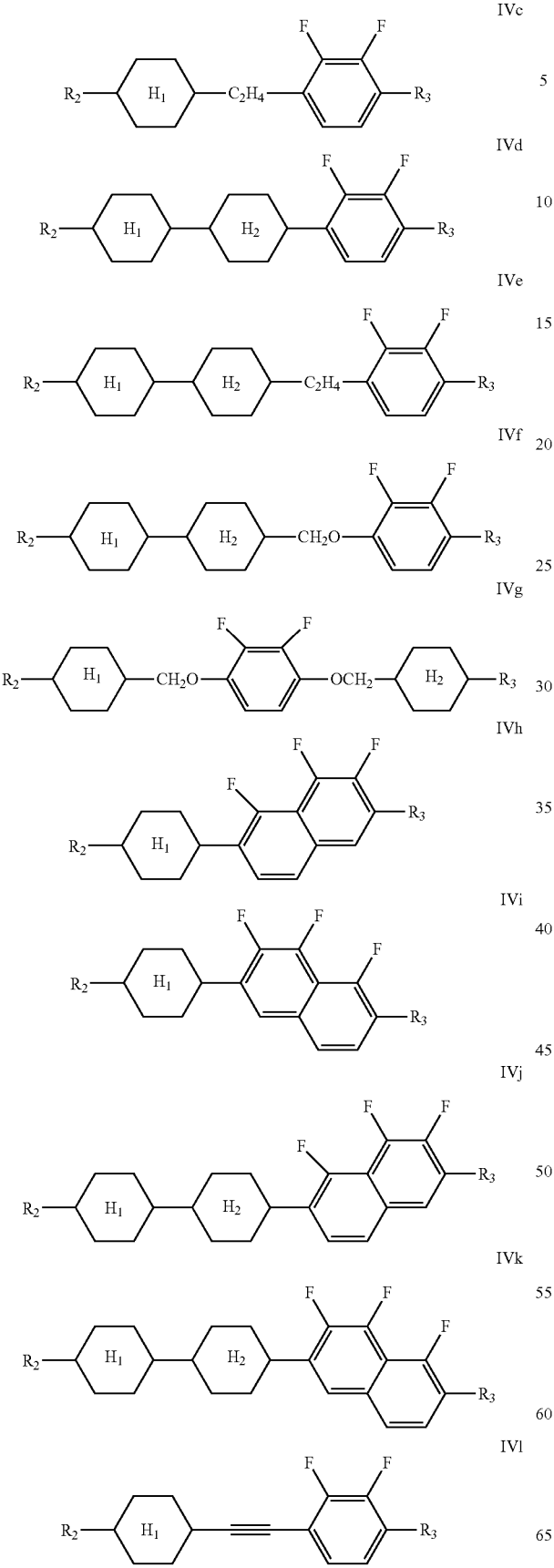

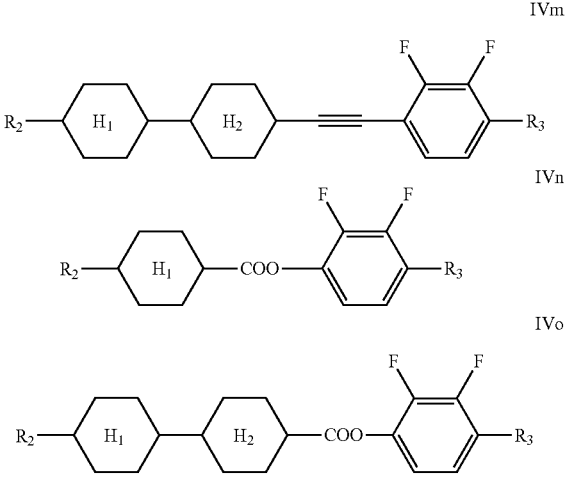

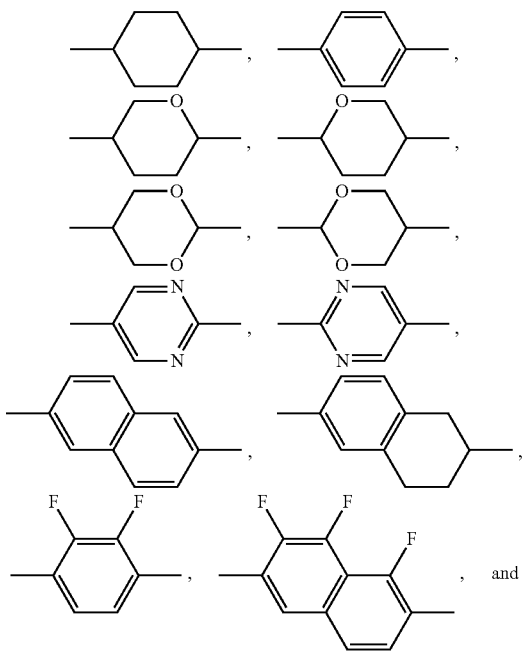

wherein $R_2$ and $R_3$ each independently represent any one of groups as shown by (1) to (3) below:
(1) linear alkyl groups having 1-7 carbon atoms or linear alkoxy groups having 1-7 carbon atoms;
(2) groups formed by substituting one or more —$CH_2$— in any one of the groups as shown by (1) with —O—, —COO—, —OOC— or —CH=CH—; and
(3) groups formed by substituting one or more —H in any one of the groups as represented by (1) with —F, —Cl, —CH=$CH_2$ or —CH=CH—$CH_3$;

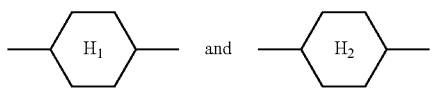

each independently represent any one of the following groups:

-continued

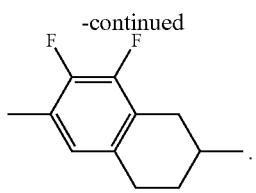

9. The liquid crystal medium according to claim 6, wherein said one or more compounds as represented by formula V are one or more of the compounds as represented by formulas Va- to Vp:

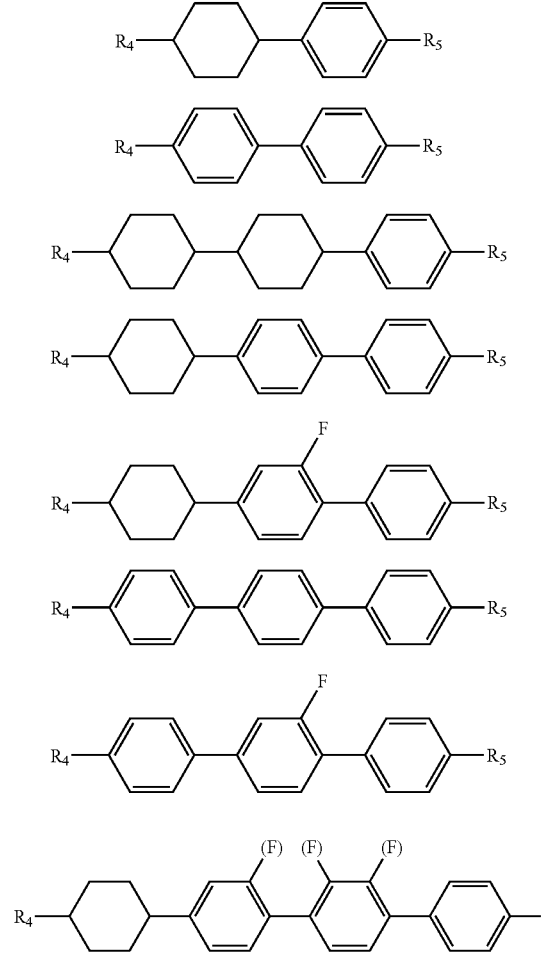

 Vi

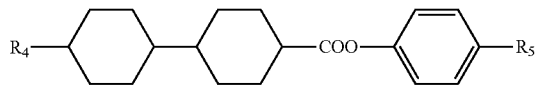 Vj

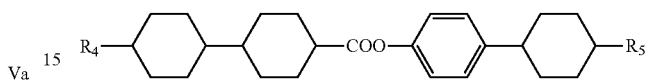 Vk

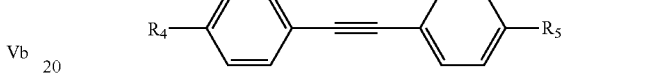 Vl

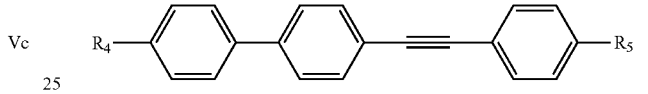 Vm

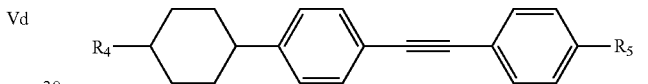 Vn

 Vo

 Vp wherein $R_4$ and $R_5$ each independently represent an alkyl group having 1-10 carbon atoms or an alkenyl group having 2-10 carbon atoms; in addition, any —$CH_2$— of these groups may be replaced with —$CH_2O$—, —$OCH_2$— or —C≡C—, and any hydrogen may be replaced with F; (F) each independently represents F or H.

* * * * *